United States Patent
Miller et al.

(10) Patent No.: US 6,672,477 B2
(45) Date of Patent: Jan. 6, 2004

(54) METHOD AND APPARATUS FOR DISPOSING OF BODILY FLUIDS FROM A CONTAINER

(75) Inventors: Mark Miller, Kiel, WI (US); Michael C. Hollen, Manitowoc, WI (US); Joseph M. Hand, Sheboygan Falls, WI (US); Barry G. Anderson, Sheboygan, WI (US)

(73) Assignee: Bemis Manufacturing Company, Sheboygan Falls, WI (US)

( * ) Notice: Subject to any disclaimer, the term of this patent is extended or adjusted under 35 U.S.C. 154(b) by 0 days.

(21) Appl. No.: 10/044,433

(22) Filed: Jan. 11, 2002

(65) Prior Publication Data

US 2002/0092580 A1 Jul. 18, 2002

Related U.S. Application Data

(60) Provisional application No. 60/261,580, filed on Jan. 12, 2001.

(51) Int. Cl.[7] .................................................. B08B 9/00
(52) U.S. Cl. ..................... 222/83.5; 222/88; 222/148; 222/181.1; 222/1; 141/1; 141/91; 141/330; 141/352; 141/364; 141/375; 141/383; 141/386
(58) Field of Search ........................... 222/83, 83.5, 88, 222/148, 181.1, 181.2, 181.3, 335, 1; 141/1, 91, 329, 330, 351–354, 363–366, 375, 383, 386, 67

(56) References Cited

U.S. PATENT DOCUMENTS

| | | |
|---|---|---|
| 1,421,325 A | 6/1922 | Walker et al. |
| 1,693,885 A | 12/1928 | Butterworth |
| 1,827,085 A | 10/1931 | Huff |
| 2,004,027 A | 6/1935 | Baxter |
| 2,009,400 A | 7/1935 | Hapgood |
| 2,073,746 A | 3/1937 | Keller |
| 2,208,028 A | 7/1940 | Harrington |
| 2,438,769 A | 3/1948 | Thomas |
| 2,641,270 A | 6/1953 | Allen |

(List continued on next page.)

FOREIGN PATENT DOCUMENTS

| | | | |
|---|---|---|---|
| EP | 0596132 A1 | 5/1994 | |
| WO | 86023430 | 4/1986 | ............. B67C/1/04 |
| WO | WO 99/00154 | 1/1999 | |

OTHER PUBLICATIONS

Judgment in a Civil Case; *Bemis Manufacturing Company and Educator Partnership v. Dornoch Medical Systems, Inc.*, Case No. 98–C–952; United States District Court, Eastern District of Wisconsin; Decision By Court Dated Aug. 31, 2000.

Med Inc., Medical Environmental Design, Inc.; Promotional Product Material, Jan. 15, 1991.

*Primary Examiner*—J. Casimer Jacyna
(74) *Attorney, Agent, or Firm*—Michael Best & Friedrich LLP

(57) ABSTRACT

A medical apparatus for draining bodily fluid from a container, such as a suction canister. The medical apparatus can include a support area and a drainage reservoir having an inlet in communication with the support area and an outlet in communication with a drain. The drainage reservoir can collect the bodily fluid from the container before the bodily fluid flows into the drain. Some embodiments of the medical apparatus include a drainage conduit or a drainage pipe. In some embodiments, the drainage reservoir is constructed of a transparent material. The medical apparatus can include a venturi valve and, in some embodiments, the water passing through the venturi valve remains separate from the bodily fluid until the water and the bodily fluid reach the drain.

32 Claims, 15 Drawing Sheets

U.S. PATENT DOCUMENTS

| | | |
|---|---|---|
| 2,799,301 A | 7/1957 | Ballard |
| 2,886,071 A | 5/1959 | Rasmussen |
| 3,171,447 A | 3/1965 | Fowler et al. |
| 3,363,627 A | 1/1968 | Bidwell et al. |
| 3,394,831 A | 7/1968 | Bathish et al. |
| 3,482,583 A | 12/1969 | Fenn |
| 3,556,101 A | 1/1971 | Economou |
| 3,603,328 A | 9/1971 | Fenn |
| 3,646,935 A | 3/1972 | Holbrook et al. |
| 3,671,982 A | 6/1972 | Sayles |
| 3,680,560 A | 8/1972 | Pannier, Jr. et al. |
| 3,685,517 A | 8/1972 | Reynolds et al. |
| 3,699,964 A | 10/1972 | Ericson |
| 3,719,197 A | 3/1973 | Pannier, Jr. et al. |
| 3,768,478 A | 10/1973 | Fertik et al. |
| 3,780,757 A | 12/1973 | Jordan |
| 3,782,414 A | 1/1974 | Holbrook |
| 3,791,394 A | 2/1974 | Hammelmann |
| 3,863,664 A | 2/1975 | Holbrook et al. |
| 3,866,608 A | 2/1975 | Reynolds et al. |
| 3,881,486 A | 5/1975 | Fenton |
| 3,897,599 A | 8/1975 | Artzer |
| 3,916,924 A | 11/1975 | McGowan |
| 3,945,392 A | 3/1976 | Deaton et al. |
| 3,958,730 A | 5/1976 | Caldwell |
| 3,989,046 A | 11/1976 | Pannier, Jr. et al. |
| 3,995,333 A | 12/1976 | Stephens |
| 4,004,590 A | 1/1977 | Muriot |
| 4,015,603 A | 4/1977 | Kurtz et al. |
| 4,049,555 A | 9/1977 | Matherne |
| 4,053,284 A | 10/1977 | Posch |
| 4,058,412 A | 11/1977 | Knapp et al. |
| 4,084,723 A | 4/1978 | Parker |
| 4,090,635 A | 5/1978 | Nelson et al. |
| 4,108,336 A | 8/1978 | Anderson, Jr. |
| 4,112,948 A | 9/1978 | Kurtz et al. |
| 4,135,515 A | 1/1979 | Muriot |
| 4,157,718 A | 6/1979 | Baehr |
| 4,195,633 A | 4/1980 | Nehring et al. |
| 4,195,672 A | 4/1980 | Freeman |
| 4,228,798 A | 10/1980 | Deaton |
| 4,238,892 A | 12/1980 | Geiss |
| 4,245,637 A | 1/1981 | Nichols |
| 4,258,824 A | 3/1981 | Kurtz et al. |
| 4,275,732 A | 6/1981 | Gereg |
| 4,306,557 A | 12/1981 | North |
| 4,321,922 A | 3/1982 | Deaton |
| 4,341,568 A | 7/1982 | Christensen |
| 4,345,342 A | 8/1982 | Saito |
| 4,356,084 A | 10/1982 | Hatton et al. |
| 4,363,340 A | 12/1982 | Naftulin |
| 4,379,455 A | 4/1983 | Deaton |
| 4,384,580 A | 5/1983 | Leviton |
| 4,388,922 A | 6/1983 | Telang |
| 4,429,803 A | 2/1984 | Butterfield |
| 4,430,084 A | 2/1984 | Deaton |
| 4,430,085 A | 2/1984 | Ahrens |
| 4,455,140 A | 6/1984 | Joslin |
| 4,484,920 A | 11/1984 | Kaufman et al. |
| 4,516,973 A | 5/1985 | Telang |
| 4,519,427 A | 5/1985 | Ono et al. |
| 4,540,413 A | 9/1985 | Russo |
| 4,559,664 A | 12/1985 | Bohme et al. |
| 4,586,549 A | 5/1986 | White |
| 4,629,159 A | 12/1986 | Wellenstam |
| 4,631,050 A | 12/1986 | Reed et al. |
| 4,666,063 A | 5/1987 | Holoubek et al. |
| 4,673,006 A | 6/1987 | Speck |
| 4,676,281 A | 6/1987 | Nord |
| 4,676,287 A | 6/1987 | Fitzwater |
| 4,681,571 A | 7/1987 | Nehring |
| 4,685,480 A | 8/1987 | Eck |
| 4,698,060 A | 10/1987 | D'Antonio et al. |
| 4,704,106 A | 11/1987 | Shave et al. |
| 4,715,855 A | 12/1987 | D'Antonio et al. |
| 4,735,610 A | 4/1988 | Akkas et al. |
| 4,740,202 A | 4/1988 | Stacey et al. |
| 4,749,010 A | 6/1988 | Petell |
| 4,762,241 A | 8/1988 | Lang |
| 4,770,787 A | 9/1988 | Heath et al. |
| 4,781,707 A | 11/1988 | Boehringer et al. |
| 4,785,963 A | 11/1988 | Magley |
| 4,795,428 A | 1/1989 | Hwang |
| 4,795,448 A | 1/1989 | Stacey et al. |
| 4,808,159 A | 2/1989 | Wilson et al. |
| 4,809,860 A | 3/1989 | Allen |
| 4,813,563 A | 3/1989 | Ogden et al. |
| 4,820,351 A | 4/1989 | Hambleton et al. |
| 4,857,063 A | 8/1989 | Glenn |
| 4,863,446 A | 9/1989 | Parker |
| 4,865,046 A * | 9/1989 | Duran ........................ 600/575 |
| 4,867,738 A | 9/1989 | Mintz |
| 4,870,975 A | 10/1989 | Cronk et al. |
| 4,889,531 A | 12/1989 | D'Antonio et al. |
| 4,902,284 A | 2/1990 | D'Antonio et al. |
| 4,905,325 A | 3/1990 | Colditz |
| 4,913,179 A | 4/1990 | Engel et al. |
| 4,913,197 A | 4/1990 | Friedrich |
| 4,926,915 A | 5/1990 | Deussen et al. |
| 4,955,874 A | 9/1990 | Farrar et al. |
| 4,957,491 A | 9/1990 | Parker |
| 4,961,440 A | 10/1990 | Wright |
| 4,967,814 A | 11/1990 | Day, Jr. |
| 4,969,491 A | 11/1990 | Kiplinger |
| 4,972,976 A | 11/1990 | Romero |
| 5,011,470 A | 4/1991 | Kurtz et al. |
| 5,024,613 A | 6/1991 | Vasconcellos |
| 5,026,358 A | 6/1991 | Everett, Jr. et al. |
| 5,027,872 A | 7/1991 | Taylor et al. |
| 5,033,492 A | 7/1991 | Mertens et al. |
| 5,045,077 A | 9/1991 | Blake, III |
| 5,049,273 A | 9/1991 | Knox |
| 5,053,026 A | 10/1991 | Andersen et al. |
| 5,064,101 A | 11/1991 | Richter et al. |
| 5,067,950 A | 11/1991 | Broadnax, Jr. |
| 5,071,035 A | 12/1991 | Kiplinger |
| 5,078,677 A | 1/1992 | Gentelia et al. |
| 5,119,830 A | 6/1992 | Davis |
| 5,121,778 A | 6/1992 | Baker et al. |
| 5,154,712 A | 10/1992 | Herweck et al. |
| 5,185,007 A | 2/1993 | Middaugh et al. |
| 5,186,195 A | 2/1993 | Wall |
| 5,192,439 A | 3/1993 | Roth et al. |
| 5,195,994 A | 3/1993 | Dieringer |
| 5,217,038 A | 6/1993 | Pinder |
| 5,222,530 A | 6/1993 | Baker et al. |
| 5,242,434 A | 9/1993 | Terry |
| 5,273,083 A | 12/1993 | Burrows |
| 5,300,050 A | 4/1994 | Everett, Jr. et al. |
| 5,338,194 A | 8/1994 | Strohmaier |
| 5,349,995 A | 9/1994 | Perez |
| 5,351,859 A | 10/1994 | Jansen |
| 5,380,289 A | 1/1995 | Hamstreet et al. |
| 5,380,314 A * | 1/1995 | Herweck et al. ............ 604/403 |
| 5,401,262 A * | 3/1995 | Karwoski et al. ........... 604/321 |
| 5,437,836 A | 8/1995 | Yamada |
| 5,439,460 A | 8/1995 | Hoover |
| 5,460,193 A | 10/1995 | Levallois et al. |
| 5,470,324 A | 11/1995 | Cook et al. |
| 5,546,979 A | 8/1996 | Clark, II et al. |
| 5,599,331 A | 2/1997 | Hemstreet et al. |

| | | | | | | |
|---|---|---|---|---|---|---|
| 5,620,428 A | 4/1997 | Hand | | 5,837,103 A | 11/1998 | Trokhan et al. |
| 5,624,417 A | 4/1997 | Cook et al. | | 5,871,476 A | 2/1999 | Hand |
| 5,637,103 A | 6/1997 | Kerwin et al. | | 5,901,717 A | 5/1999 | Dunn et al. |
| 5,669,892 A | 9/1997 | Koegh et al. | | 5,931,822 A | 8/1999 | Bemis et al. |
| 5,678,564 A | 10/1997 | Lawrence et al. | | 6,027,490 A | 2/2000 | Radford et al. |
| 5,683,371 A | 11/1997 | Hand | | 6,244,311 B1 | 6/2001 | Hand et al. |
| 5,688,255 A | 11/1997 | Hand | | 6,263,887 B1 | 7/2001 | Dunn |
| 5,725,516 A | 3/1998 | Cook et al. | | 6,358,232 B1 | 3/2002 | Hand et al. |
| 5,741,237 A | 4/1998 | Walker | | 6,368,310 B1 | 4/2002 | Bemis et al. |
| 5,776,118 A | 7/1998 | Seifert et al. | | 2002/0029793 A1 | 3/2002 | Dunn et al. |
| 5,776,260 A | 7/1998 | Dunn et al. | | | | |
| 5,807,359 A | 9/1998 | Bemis et al. | | * cited by examiner | | |

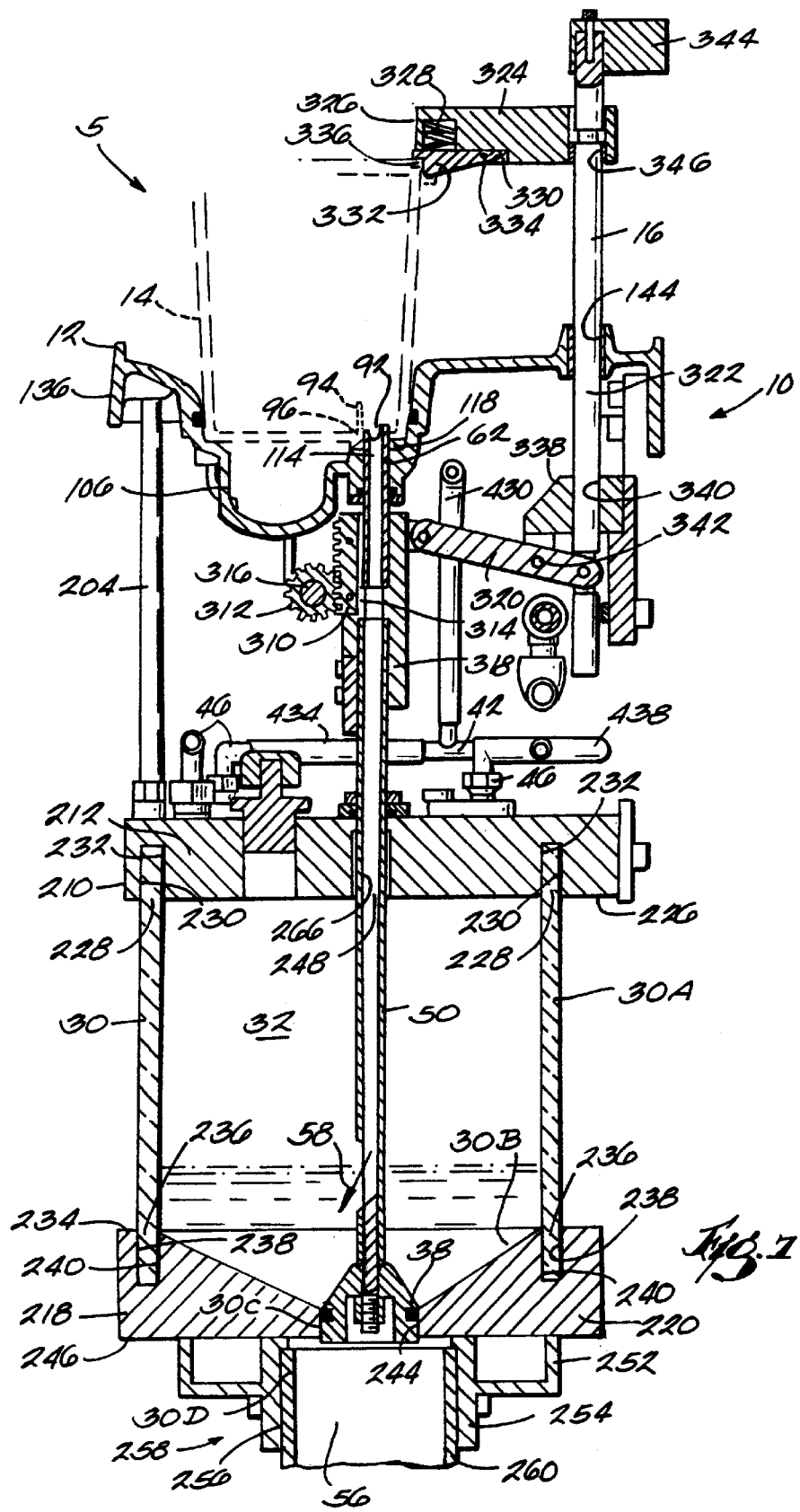

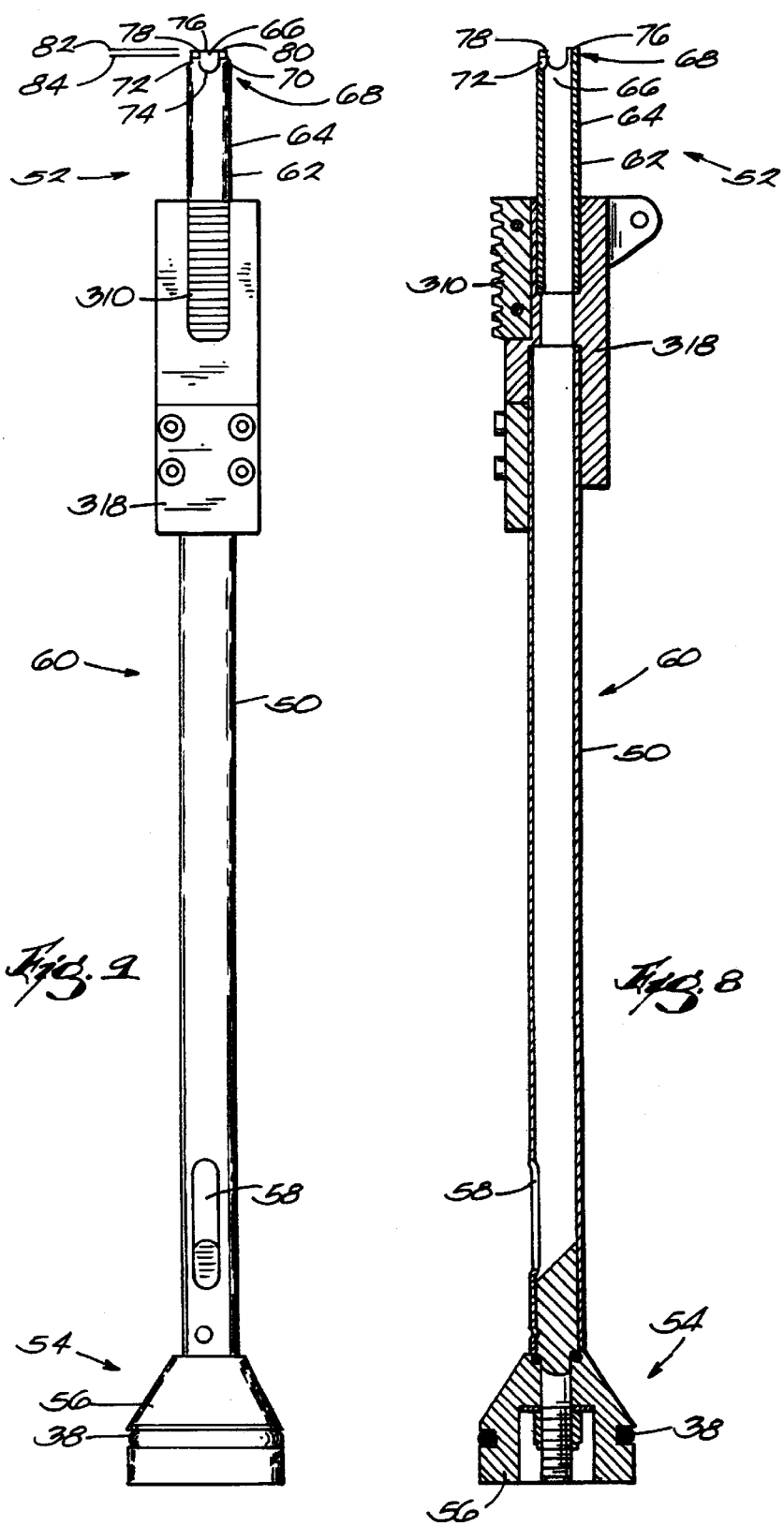

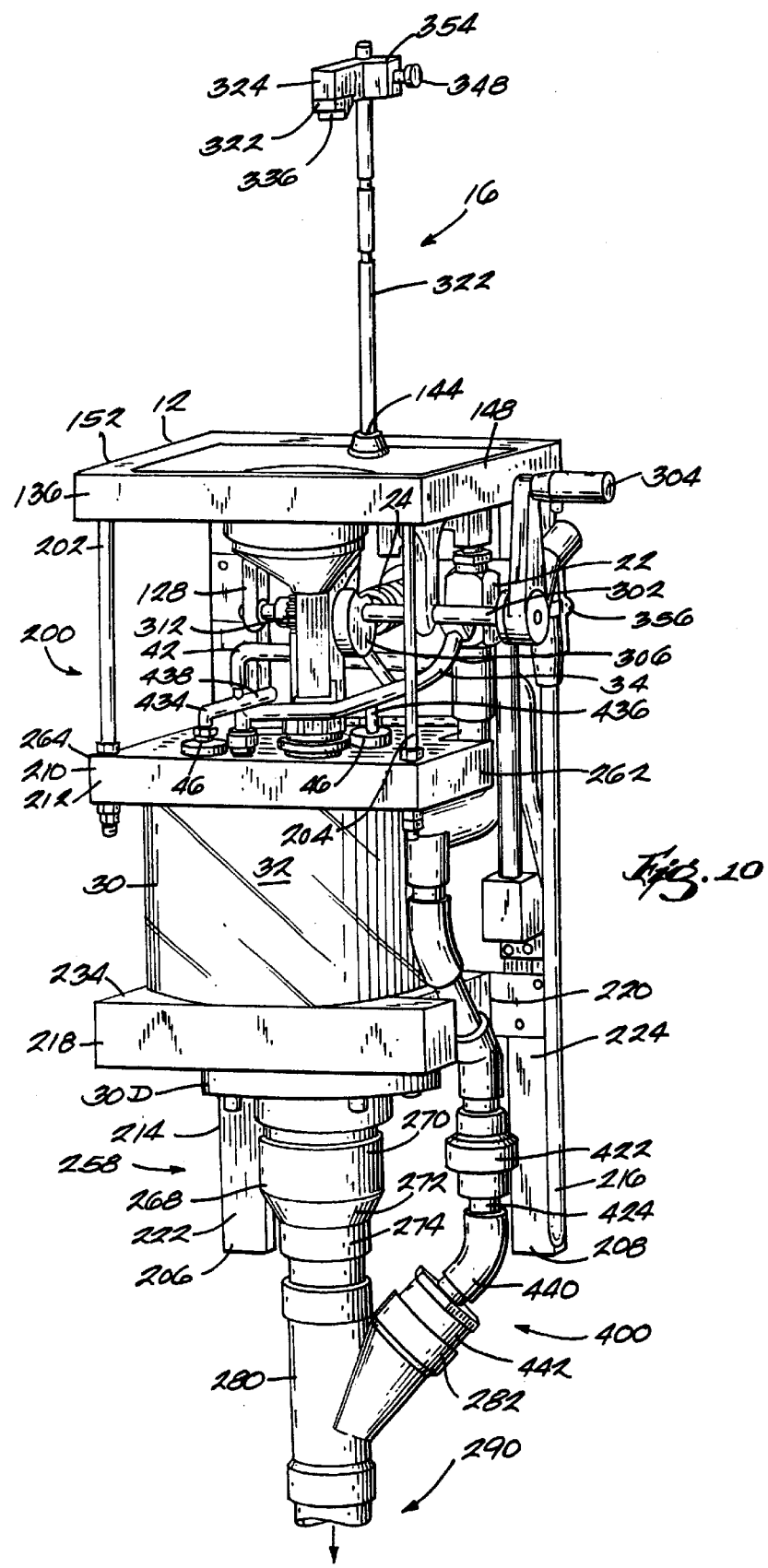

METHOD AND APPARATUS FOR DISPOSING OF BODILY FLUIDS FROM A CONTAINER

RELATED APPLICATIONS

Priority is claimed under 35 U.S.C. §119 to U.S. patent application Ser. No. 60/261,580 filed Jan. 12, 2001.

FIELD OF THE INVENTION

The invention relates to a method and apparatus for draining bodily fluid held in a container such as a suction canister.

BACKGROUND OF THE INVENTION

Containers, such as suction canisters, are used in hospital environments and particularly during various surgical procedures to store bodily fluid drained from a patient. In general, suction canisters are used in conjunction with a vacuum source which enables bodily fluid to be drained from the patient and stored in the canister. Each suction canister generally includes a receptacle for holding the bodily fluid, a lid with a vacuum port and a patient port, a suction conduit connecting the vacuum port to a vacuum source, and a patient conduit for conveying the bodily fluid from the patient into the receptacle through the patient port. When the suction conduit is connected to the vacuum source, a negative pressure gradient is created in the interior of the receptacle so that the bodily fluid is drawn from the patient and into the suction canister via the patient conduit.

Other types of containers, such as urine collectors and chest drainage devices, can also be used to collect body fluids.

It has become important in environments such as hospitals to eliminate the handling of and thus reduce employee exposure to bodily fluids. Hospitals dispose of such bodily fluid in various ways. Bodily fluid can be poured from the suction canister down the hospital sink and into the sanitary sewer system, can be incinerated as a liquid or solid, or can be disposed of at an approved hazardous waste site. However, if hospital employees have to handle the bodily fluid, spattering of the bodily fluid can result in hospital employees contacting the hazardous fluid.

SUMMARY OF THE INVENTION

A continuing need exists for a method and apparatus for draining and disposing of bodily fluid so that hospital employees do not have to handle or come into contact with the bodily fluid.

Accordingly, the invention provides a method and apparatus for draining and disposing of bodily fluid so that hospital employees do not have to handle the bodily fluid. The method and apparatus are particularly suited for use with containers, such as suction canisters, having a drain port in the bottom wall of the container. A container filled with bodily fluid needing to be drained is positioned on a drain station. The user actuates a mechanism, such as a handle, which opens the drain port and allows the bodily fluid to flow out of the container and preferably into a sanitary sewer system.

More particularly, the invention provides a medical apparatus for draining bodily fluid held in a container. The medical apparatus includes a support area that is adapted to removably support the container and a drainage reservoir having an inlet in communication with the support area and an outlet in communication with a drain. The drain preferably leads to a sanitary sewer system. The drainage reservoir is adapted to collect the bodily fluid drained from the container before the bodily fluid flows into the drain.

The invention also provides a method of draining bodily fluid from a container including positioning the container in a support area that is adapted to removably support the container, draining the bodily fluid from the container, collecting the bodily fluid drained from the container into a drainage reservoir, and releasing the bodily fluid collected in the drainage reservoir into a drain.

The invention further provides a medical apparatus including a support area that is adapted to removably support a container, a drainage reservoir having an inlet in communication with the support area and an outlet in communication with a drain, and a drainage conduit positioned adjacent the drainage reservoir. The drainage conduit has a first end movably positioned in the inlet. The first end includes a tool that is actuable to alter the container such that the bodily fluid held in the container drains from the container. The drainage conduit has a second end including a reservoir plug removably positioned in the outlet in order prevent the bodily fluid from flowing out of the drainage reservoir and into the drain.

The invention further provides a method of draining bodily fluid from a container including positioning the container in a support area that is adapted to removably support the container and moving a drainage conduit into a first position in which a tool coupled to a first end of the drainage conduit alters the container and a reservoir plug coupled to a second end of the drainage conduit is positioned in an outlet of a drainage reservoir, so that the bodily fluid drains from the container and is collected in the drainage reservoir. The method also includes moving the drainage conduit into a second position in which the reservoir plug is removed from the outlet, so that the bodily fluid flows from the drainage reservoir into a drain.

The invention further provides a medical apparatus including a support area that is adapted to removably support a container, a drainage reservoir having an inlet in communication with the support area and an outlet, and a drainage pipe in communication with the outlet of the drainage reservoir. At least a portion of the drainage pipe has a diameter greater than the diameter of the outlet.

The invention further provides a medical apparatus including a support area that is adapted to removably support the container and a drainage reservoir in communication with the support area. The drainage reservoir is adapted to collect the bodily fluid drained from the container and is constructed of a transparent material, so that the bodily fluid being collected in the drainage reservoir can be viewed from outside of the drainage reservoir.

The invention further provides a medical apparatus including a support area that is adapted to removably support a container, a drainage reservoir in communication with the support area and a drain, and a venturi valve coupled between a water supply and the drain. The venturi valve is in communication with the drainage reservoir to generate a vacuum in order to drain the bodily fluid from the container. The water passing through the venturi valve remains separate from the bodily fluid passing through the drainage reservoir until the water and the bodily fluid reach the drain.

The invention further provides a method of draining bodily fluid from a container including positioning the container in a support area that is adapted to removably support the container and providing a drainage reservoir in communication with the support area and a drain. The method also includes generating a vacuum in the drainage reservoir by passing water through a venturi valve in communication with the drainage reservoir in order to drain the bodily fluid from the container into the drainage reservoir. The method further includes releasing the bodily fluid from the drainage reservoir into the drain and preventing the water passing through the venturi valve from mixing with the bodily fluid until the water and the bodily fluid reach the drain.

The invention further provides a medical apparatus including a support area that is adapted to removably support a container, a drainage reservoir having an inlet in communication with the support area in order to receive the bodily fluid drained from the container and an outlet, and a drainage pipe in communication with the outlet of the drainage reservoir in order to release the bodily fluid from the drainage reservoir into a drain. The bodily fluid flows in a single direction through the support area, the drainage reservoir, and the drainage pipe and into the drain without flowing through any check valves.

Other features and advantages of the invention will become apparent to those of ordinary skill in the art upon review of the following description and drawings.

BRIEF DESCRIPTION OF THE DRAWINGS

FIG. 7 is a side sectional view of the medical apparatus with the drain conduit in a second position;

FIG. 8 is a sectional view of the drain conduit;

FIG. 9 is a side elevational view of the drain conduit;

FIG. 10 is a perspective view of the medical apparatus with a cabinet cover removed;

Figure 1:
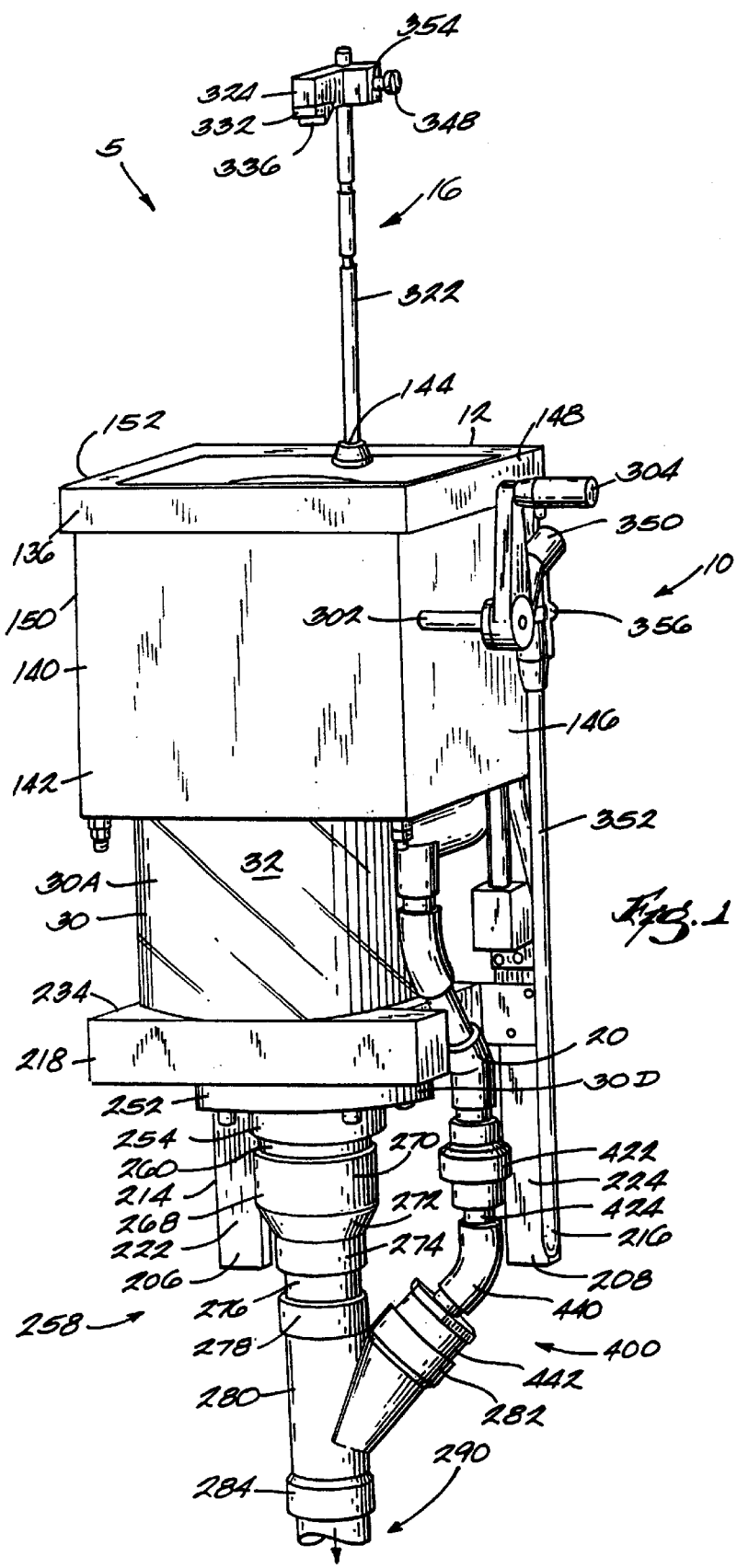
FIG. 1 is perspective view of a medical apparatus embodying the invention.
Figure 2:
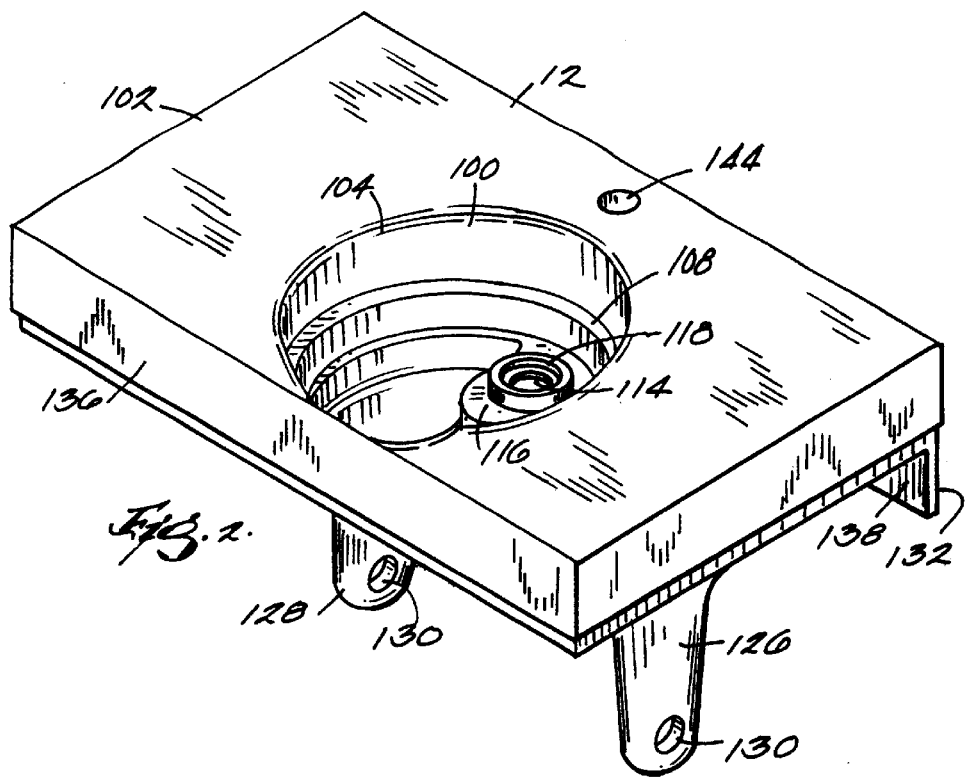
FIG. 2 is a perspective view of a casting for use with the medical apparatus.
Figure 3:
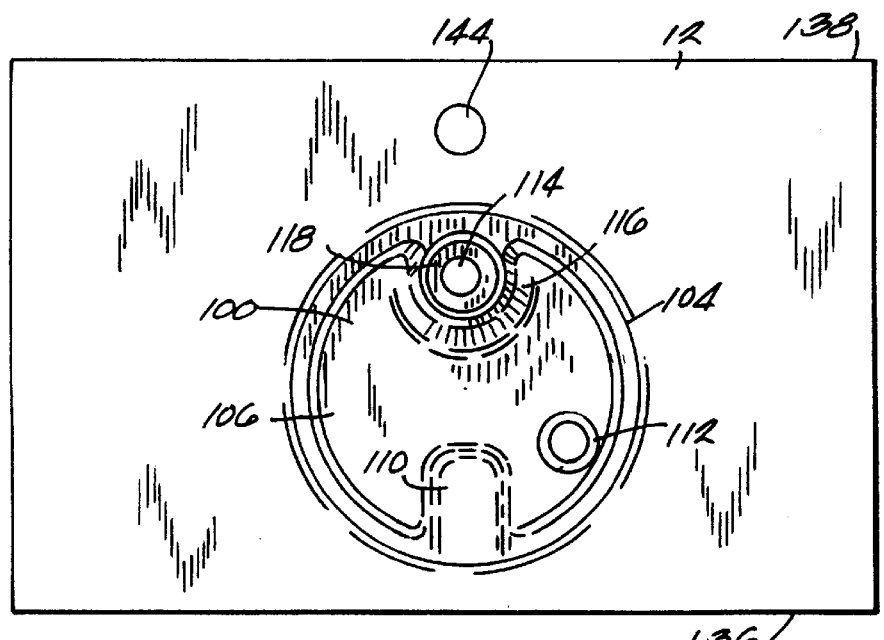
FIG. 3 is a plan view of the casting.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DESCRIPTION OF THE PREFERRED EMBODIMENT

Figure 5:
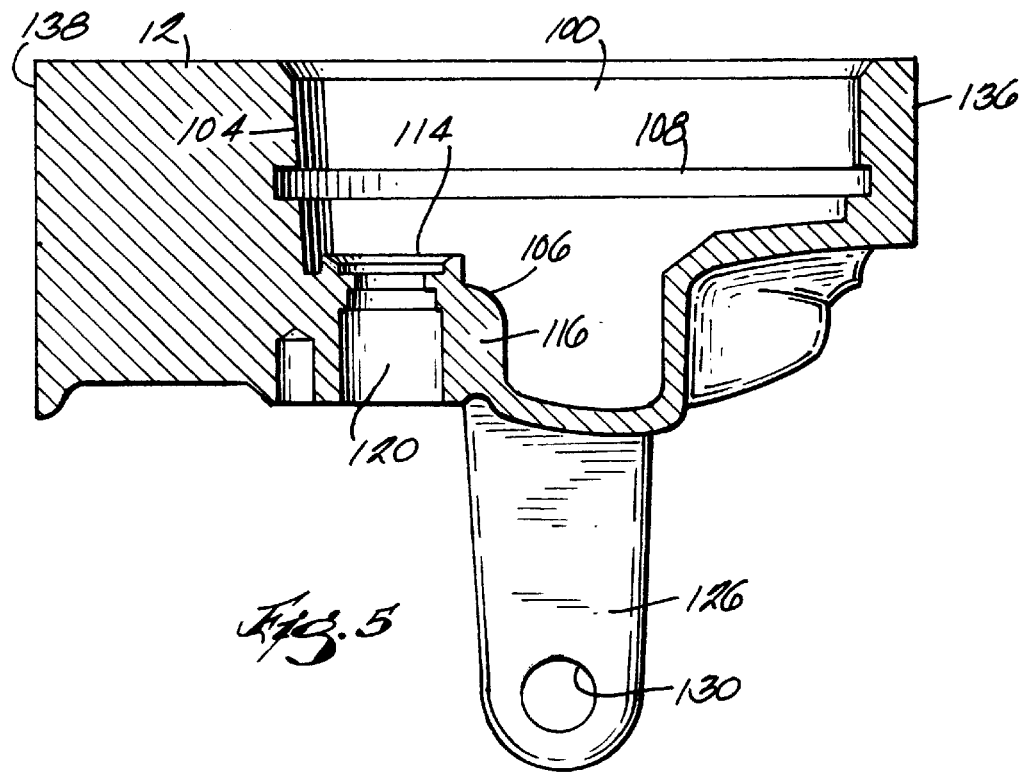
FIG. 5 is a view taken along line 5—5 of FIG. 4.
Figure 6:
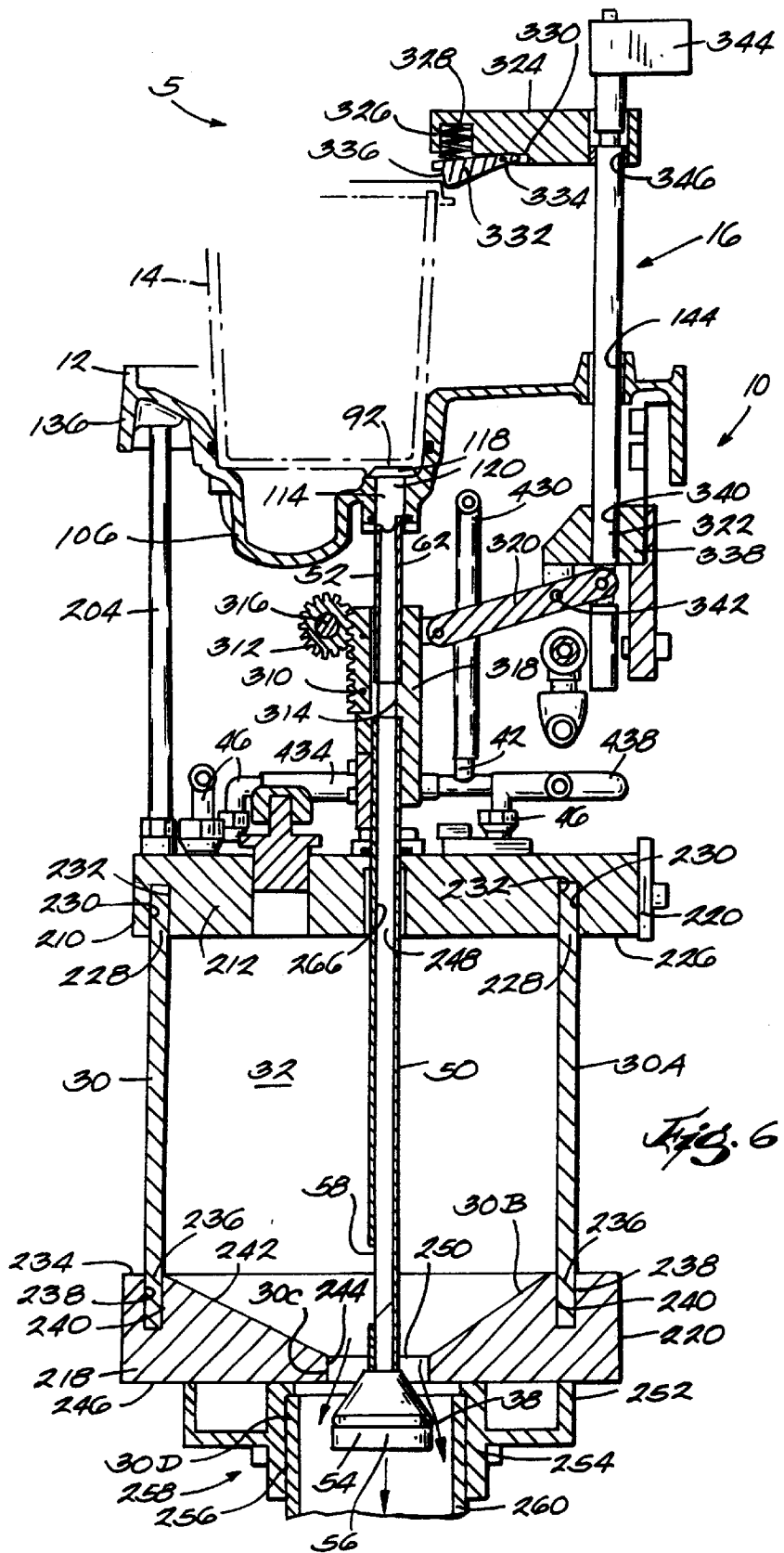
FIG. 6 is a side sectional view of the medical apparatus with a drain conduit in a first position.
Figure 11:
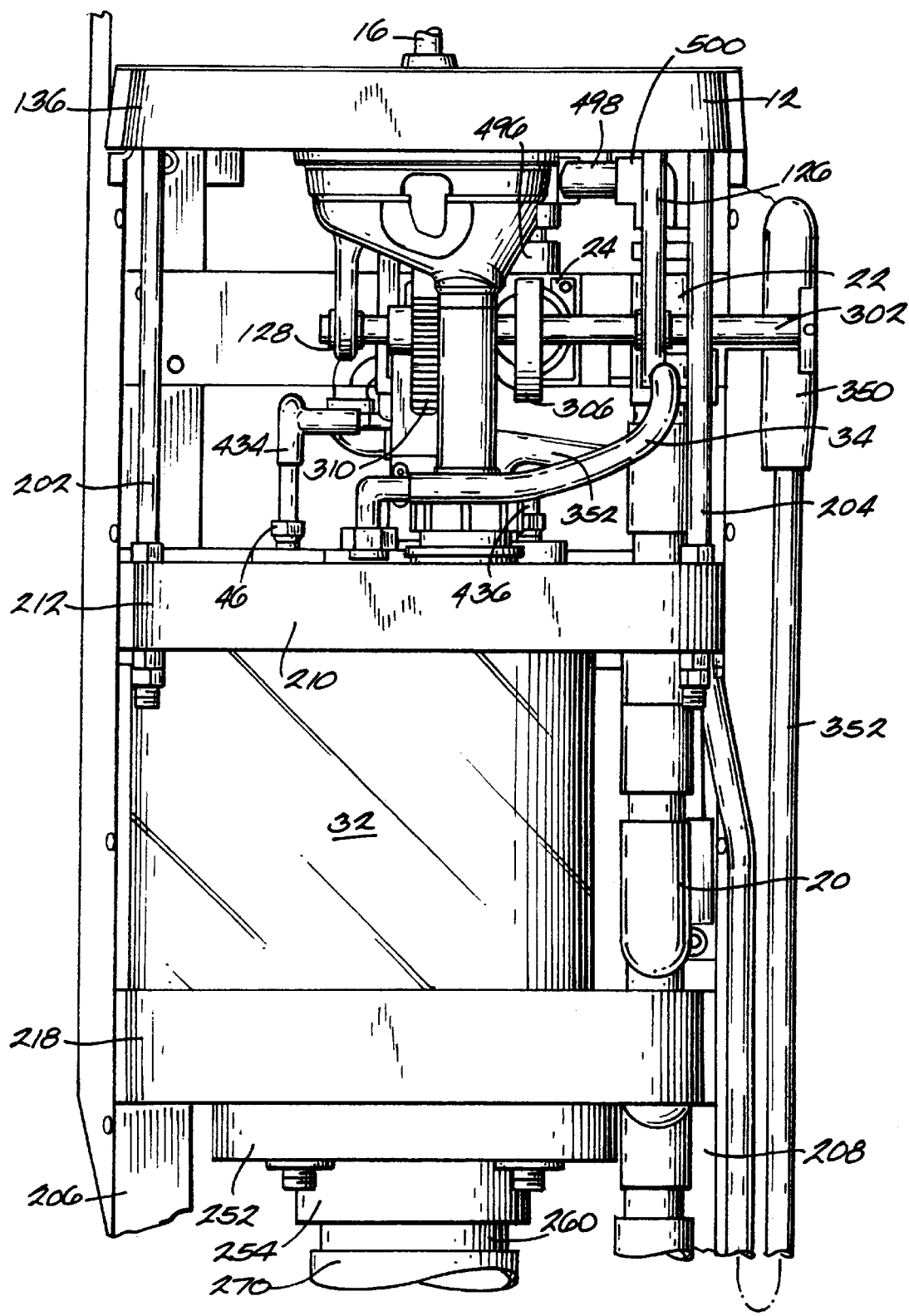
FIG. 11 is front sectional view of the medical apparatus with the cabinet cover removed.

Referring now to the drawings in which like reference numerals refer to like parts throughout the views, there is shown in FIGS. 1 through 18 a medical apparatus 5 embodying the invention. The medical apparatus 5 comprises a drain station 10. As shown in FIGS. 1, 6, and 7, the drain station 10 includes a casting 12 that is adapted to house a container 14. Preferably, the container 14 is a suction canister; however, it should be noted that other types of containers that are designed to contain bodily fluid can also be used in conjunction with the drain station 10. Preferably, the container 14 includes a normally-closed, drain port 92 in the bottom wall of the container 14. An example of such a container 14 can be found in U.S. Pat. No. 5,688,255, which is hereby incorporated by reference.

The casting 12 is shown in FIGS. 2 through 5. The casting 12 includes a container support area, such as central recess 100 in a top surface 102. It should be noted that the support area could have other configurations to removably support the container 14. The recess 100 is designed to house and support the container 14. The recess 100 is defined by an annular wall 104 and a bottom wall 106. A lip seal 108 is housed in the wall 104, and preferably in a groove in the wall 104 to prevent the seal 108 from being dislodged as containers are inserted and removed from the recess 100. The seal 108 provides a air-tight seal when a container 14 is being drained to prevent any fluid draining from the container 14 from contacting the user.

A key 110 extends inwardly from the wall 104. The key 110 cooperates with a keyway (not shown) in the container 14, so as to properly oriented the container 14 relative to the casting 12. An emergency drain port 112 is also provided in the bottom wall 106. A drain port 114 is provided in the bottom wall 106 on a raised portion 116 of the bottom wall 106 that is spaced from the emergency drain port 112. A gasket 118 is positioned above the drain port 114. A drain passageway 120 (as best shown in FIG. 5) is provided in the casting 12 in communication with the drain port 114. The casting 12 also includes two downwardly extending legs 126 and 128 that have therein axially aligned apertures 130.

Figure 4:
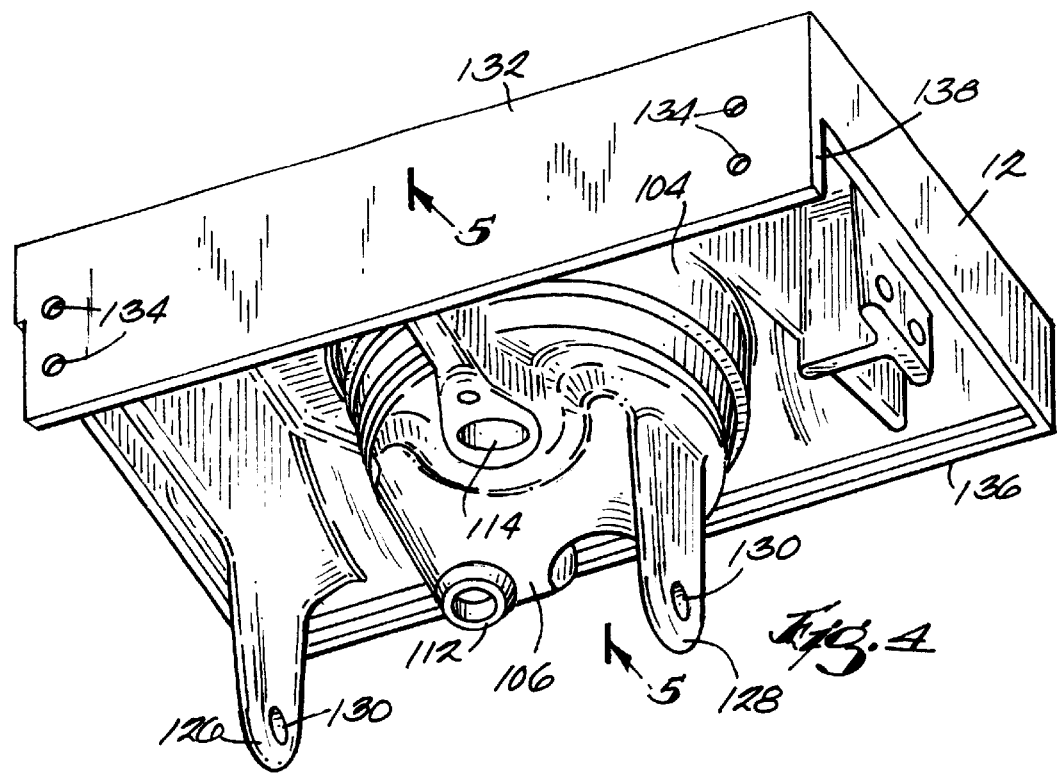
FIG. 4 is bottom perspective view of the casting.

The casting 12 is supported by a housing 200. As shown in FIG. 10, the housing 200 includes two front vertical support members 202 and 204 and two rear vertical support members 206 and 208. A first or top end of each of the front support members 202 and 204 is coupled to the casting 12 near a front edge 136 of the casting 12. A second or bottom end of each of the support members 202 and 204 is coupled to a front edge 210 of a first horizontal support member 212. A first or top end of each of the rear support members 206 and 208 is coupled to a mounting surface 132 of the casting 12 through holes 134 (as shown in FIG. 4). The rear support members 206 and 208 are preferably substantially longer than the front support members 202 and 204. The first horizontal support member 212 is coupled to the rear support members 206 and 208 approximately one-third of the way down the length of the support members 206 and 208 from the casting 12. The rear support members 206 and 208 include mounting surfaces 214 and 216, respectively, which may be mounted to the wall (e.g., via brackets, screws, and the like that are positioned through the rear support members 206 and 208 and secured to the wall). Although the housing 200 is described as being mounted to a wall, the drain station 10 may also be a free-standing unit.

Referring to FIGS. 1 and 10, a cabinet cover 140 preferably having three panels is removably mounted to the casting 12 and to the first horizontal support member 212 in order to cover and protect the internal components of the drainage station 10. Specifically, a first panel 142 is coupled between the front edge 136 of the casting 12 and the front vertical support members 202 and 204. The first panel 142 is also coupled to the front edge 210 of the first horizontal support member 212. A second panel 146 is coupled between a side edge 148 of the casting 12 and the front vertical support member 204 and the rear vertical support member 208. The second panel 146 is also coupled to a side edge 262 of the first horizontal support member 212. Finally, a third panel 150 is coupled between a side edge 152 of the casting 12 and the front vertical support member 202 and the rear vertical support member 206. The third panel 150 is also coupled to a side edge 264 of the first horizontal support member 212. The panels 142, 146, and 150 may be hingeably or rigidly coupled to one another to form the cabinet cover 140 and may be removably mounted to the drainage station 10 in any conventional manner, such as with bolts or screws for example.

Referring to FIGS. 1, 6, and 7, the drain station 10 further includes a waste trap, referred to hereinafter as a drainage reservoir 30. The drainage reservoir 30 includes a main upper portion 30A having an interior 32, a tapered portion 30B, a reduced-diameter portion 30C below the tapered portion 30B, and an enlarged portion 30D (enlarged relative to the reduced-diameter portion 30C) below the reduced-diameter portion 30C. Preferably, at least the main upper portion 30A of the drainage reservoir 30 is constructed of a transparent material, such as transparent plastic or glass, so that a user can view the bodily fluid contained in the drainage reservoir 30 from outside of the drainage station 10. Thus, the user can periodically check that the bodily fluid draining from the container 14 is properly draining into and collecting in the drainage reservoir 30. For example, if multiple containers 14 are being drained, the user can check to see if the drainage reservoir 30 is full before draining another container 14. Also, the user can check to see if the drain station 10 needs to be cleaned. Moreover, the user is able to inspect any potentially clogged areas in the drain station 10.

The housing 200 also includes a second horizontal support member 218 used to position and support the drainage reservoir 30. As shown in FIGS. 1 and 10, a back edge 220 of the second horizontal support member 218 is coupled to a front surface 222 and 224 of each of the rear support members 206 and 208, respectively.

As shown in FIGS. 6 and 7, the drainage reservoir 30 is positioned between the first horizontal support member 212 and the second horizontal support member 218. The first horizontal support member 212 includes an annular wall 266 which defines an inlet 248 into the interior 32 of the drainage reservoir 30. Also, a bottom side 226 of the first horizontal support member 212 includes an annular recess 228 comprised of a first annular wall 230 having a larger diameter than a second annular wall 232. Similarly, a top side 234 of the second horizontal support member 218 includes an annular recess 236 comprised of a first annular wall 238 having a larger diameter than a second annular wall 240. A top surface of the main upper portion 30A of the drainage reservoir 30 is positioned within the annular recess 228 in the first horizontal support member 212, and a bottom surface of the main upper portion 30A of the drainage reservoir 30 is positioned within the annular recess 236 in the second horizontal support member 218. The top side 234 of the second horizontal support member 218 also includes a tapered recess 242 which forms the tapered portion 30B of the drainage reservoir 30. Also, the second horizontal support member 218 includes an annular wall 244 extending from the tapered recess 242 through to a bottom side 246 of the second horizontal support member 218. The annular wall 244 forms an outlet 250 for the drainage reservoir 30.

The bottom side 246 of the second horizontal support member 218 is coupled to the enlarged-portion 30D of the drainage reservoir 30. The enlarged-portion 30D includes a first portion 252 coupled to the bottom side 246 of the second horizontal support member 218 in order to encompass the outlet 250. The enlarged-portion 30D also includes a second portion 254 coupled to the first portion 252 and having a smaller outer diameter than the first portion 252. An annular wall 256 having a single diameter is defined through both the first portion 252 and the second portion 254.

The annular wall 256 is coupled to an upper drainage assembly 258, which includes a first fitting 260. A first end of the first fitting 260 is coupled to the annular wall 256 of the enlarged-portion 30D of the drainage reservoir 30. Preferably, the inner diameter of the first fitting 260 is greater than the diameter of the annular wall 244 which defines the outlet 250, so that the bodily fluid that flows through the outlet 250 is not further restricted upon entering and flowing through the first fitting 260.

Referring to FIGS. 1 and 10, a second end of the first fitting 260 is coupled to a reducer coupling 268. The reducer coupling 268 includes a first portion 270, a tapered portion 272, and a second portion 274 having a smaller diameter than the first portion 270. Preferably, the diameters of each of the portions 270, 272, and 274 are also greater than the diameter of the outlet 250, so that the bodily fluid that flows through the outlet 250 is not further restricted upon entering and flowing through the reducer coupling 268.

Figure 15:
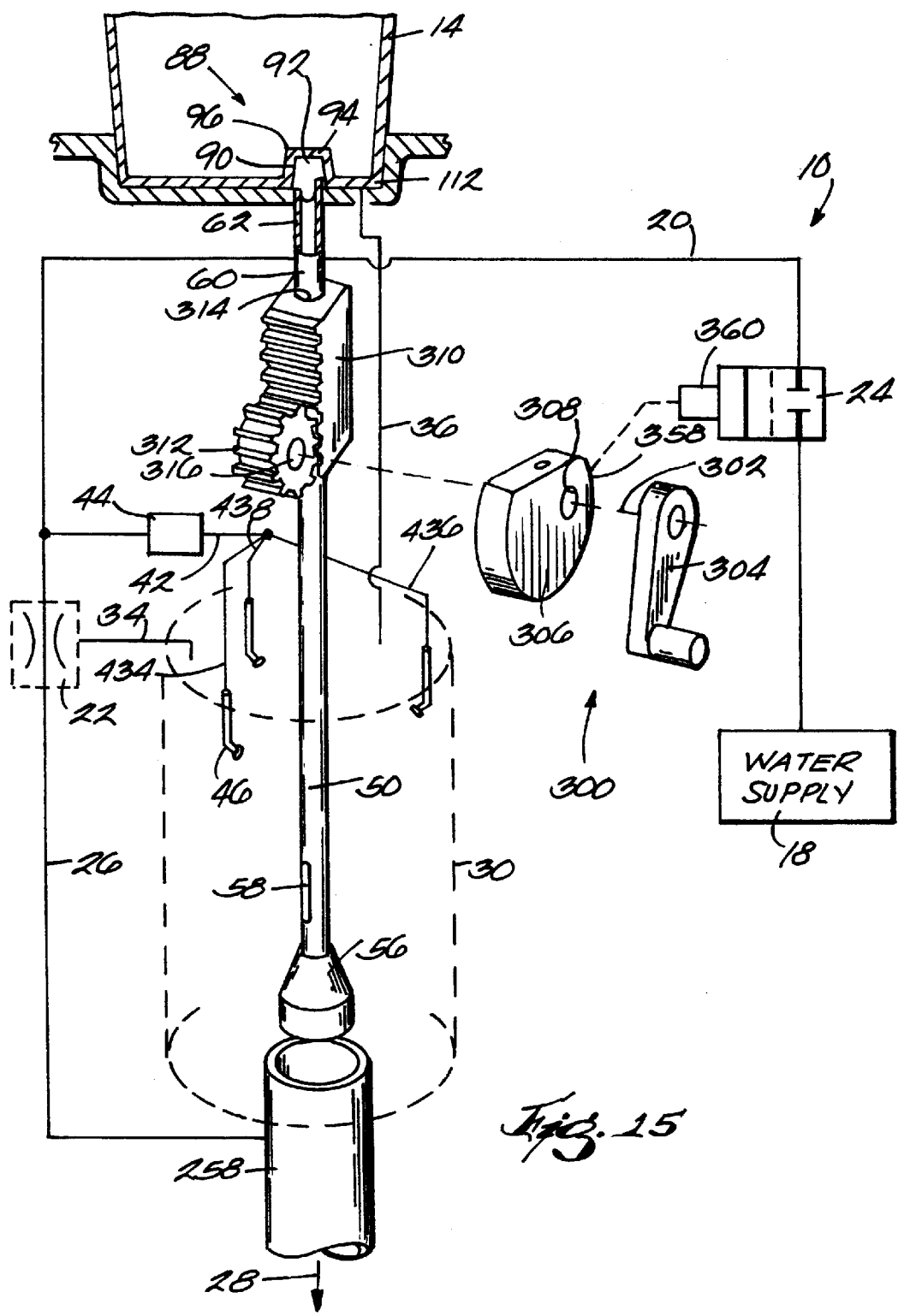
FIG. 15 is a schematic illustration of the cam assembly coupled to the medical apparatus.
Figure 16:
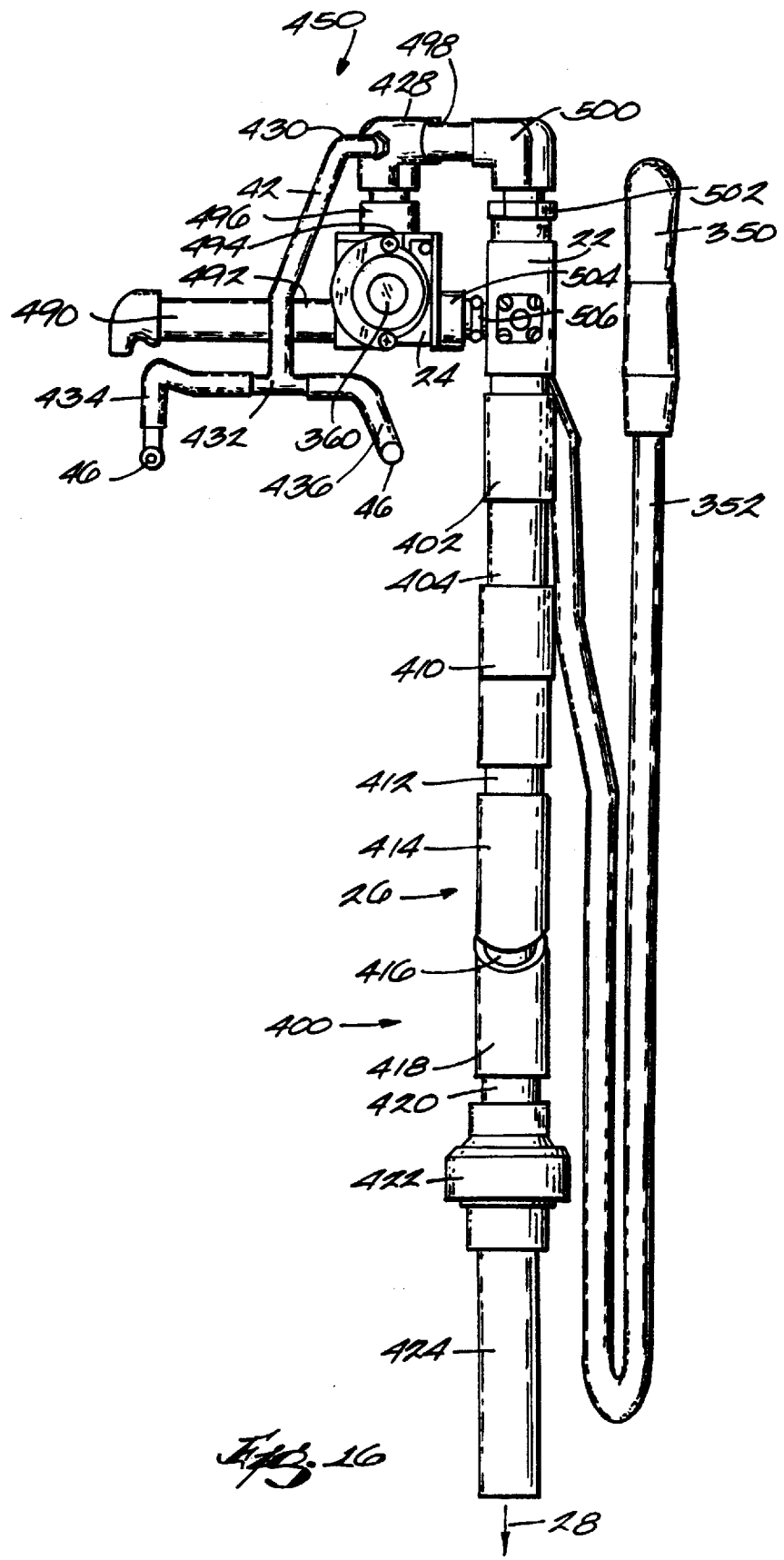
FIG. 16 is a front view of a water supply plumbing assembly and a water drainage plumbing assembly for use with the medical apparatus.
Figure 17:
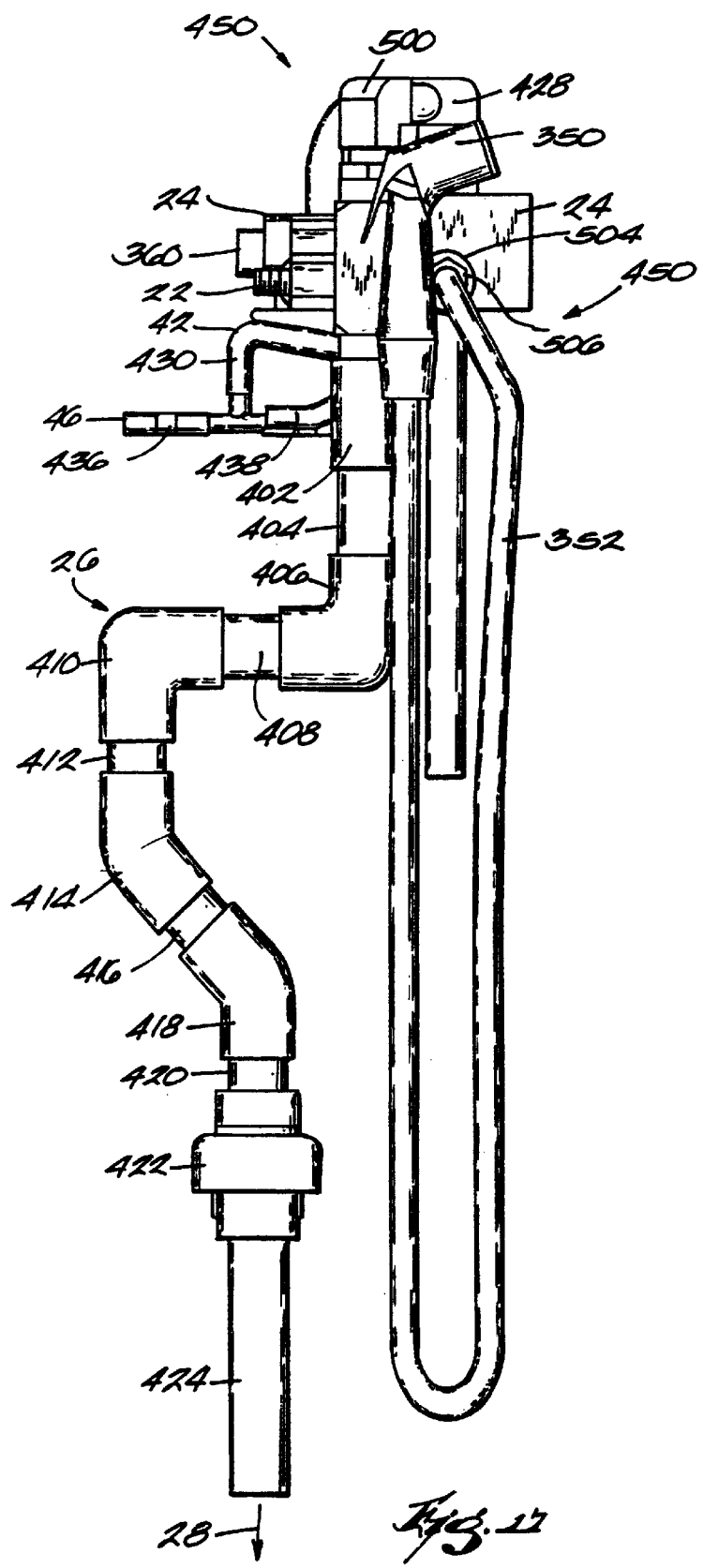
FIG. 17 is a side view of the water supply plumbing assembly and the water drainage plumbing assembly.

The second portion 274 of the reducer coupling 268 is coupled to one end of a second fitting 276. The other end of the second fitting 276 is coupled to a first input 278 of a wye connector 280. A second input 282 of the wye connector 280 is coupled to a water drainage plumbing assembly 400, as will be described in detail below. An output 284 of the wye connector 280 is coupled to a lower drainage pipe assembly 290. The lower drainage pipe assembly 290 may be comprised of any number of pipes, fittings, couplings, and the like in order to provide communication between the drainage station 10 and a sanitary sewer system 28 (as indicated in FIGS. 15–17).

As shown in FIGS. 6 and 7, the drain station 10 further includes a main drain line, such as a drain conduit 50, which is preferably positioned substantially within the interior 32 of the drainage reservoir 30. As best shown in FIGS. 8 and 9, the drain conduit 50 includes a first or upper end 52, a main drain conduit portion 60, and a second or lower end 54. As shown in FIGS. 6 and 7, the upper end 52 of the drain conduit 50 is in communication with the passageway 120 of the casting 12 and is adapted to engage and open the container 14, such as by punching or piercing the container 14 or other such action, after which bodily fluid flows out of the container 14 via the drain conduit 50.

Referring to FIGS. 8 and 9, the upper end 52 of the drain conduit 50 preferably includes a tool 62. The tool 62 includes a cylindrical wall 64 which defines a central passageway 66. The wall 64 terminates in an end surface 68 such that the passageway 66 is accessible from the end surface 68. The tool 62 includes three generally U-shaped recesses 70, 72, and 74 in the wall 64 and adjacent to the end surface 68. A first portion 76 of the wall 64 is located between the recess 70 and the recess 72. A second portion 78 of the wall 64 is located between the recess 72 and the recess 74. A third portion 80 of the wall 64 is located between the recess 70 and the recess 74. Preferably, the first portion 76 includes more of the circumference of the end surface 68 of the wall 64 than do the second or third portions 78 or 80, respectively.

The first portion 76 does not terminate in a common plane with the second or third portions 78 or 80, respectively. Instead, the first portion 76 terminates in a first plane 82 and the second and third portions 78 and 80, respectively, terminate in a second plane 84. The portions 76, 78, and 80 of the tool 62 are adapted to alter the container 14, so that the bodily fluid held within the container 14 can drain from the container 14.

The main conduit portion 60 of the drain conduit 50 is coupled to the tool 62 and provides communication between the casting 12 and the interior 32 of the drainage reservoir 30. Specifically, the main conduit portion 60 is movably positioned within the annular wall 266 of the inlet 248 of the drainage reservoir 30. The main conduit portion 60 includes a cutout portion 58 that allows the bodily fluid to exit the central passageway 66 of the drainage conduit 50 and flow into the interior 32 of the drainage reservoir 30. Preferably, the cutout portion 58 has an elongated-oval shape, as shown in FIG. 8. Also, the cutout portion 58 is preferably orientated within the drainage reservoir 30 so that the bodily fluid flowing out of the cutout portion 58 can be viewed through the transparent upper portion 30A of the drainage reservoir 30. Thus, the user can periodically check the flow of bodily fluid through the cutout portion 58 in order to see if the cutout portion 58 is clogged.

The lower end 54 of the drain conduit 50 is connected to a reservoir plug 56 that includes a gasket or O-ring 38. Referring to FIGS. 6 and 7, the reservoir plug 56 acts like a piston by being selectively moveable into and out of a sealing relationship with the annular wall 244 of the second horizontal support member 218, which defines the reduced-diameter portion 30B of the drainage reservoir 30. When the reservoir plug 56 is positioned in the reduced-diameter portion 30B, bodily fluid held in the interior 32 of the drainage reservoir 30 cannot flow through the outlet 250. When the reservoir plug 56 is removed from the reduced-diameter portion 30B, bodily fluid held in the interior 32 of the drainage reservoir 30 can flow through the outlet 250.

The drain conduit 50 is movable between a first or initial position and a second or operating position. In the first position as shown in FIG. 6, the tool 62 is positioned within the drain passageway 120 of the casting 12, but the tool 62 is not in communication with the bottom of the container 14. Also in the first position, the reservoir plug 56 is not positioned in a sealing relationship with the annular wall 244 that defines the outlet 250 of the drainage reservoir 30. Accordingly, in the first position, any bodily fluid held within the drainage reservoir 30 flows out of the outlet 250.

As will be described in more detail below, the drain conduit 50 is actuated from the first position to the second position in order for the tool 62 to alter the container 14. In the second position as shown in FIG. 7, the tool 62 is positioned within the drain passageway 120 of the casting 12 and is in communication with the interior of the container 14. Also in the second position, the reservoir plug 56 is positioned in a sealing relationship with the annular wall 244 that defines the outlet 250 of the drainage reservoir 30. Accordingly, in the second position, the bodily fluid drains out of the container 14, through the central passageway 66 of the tool 62, through the cutout portion 58, and collects in the drainage reservoir 30.

Figure 14:
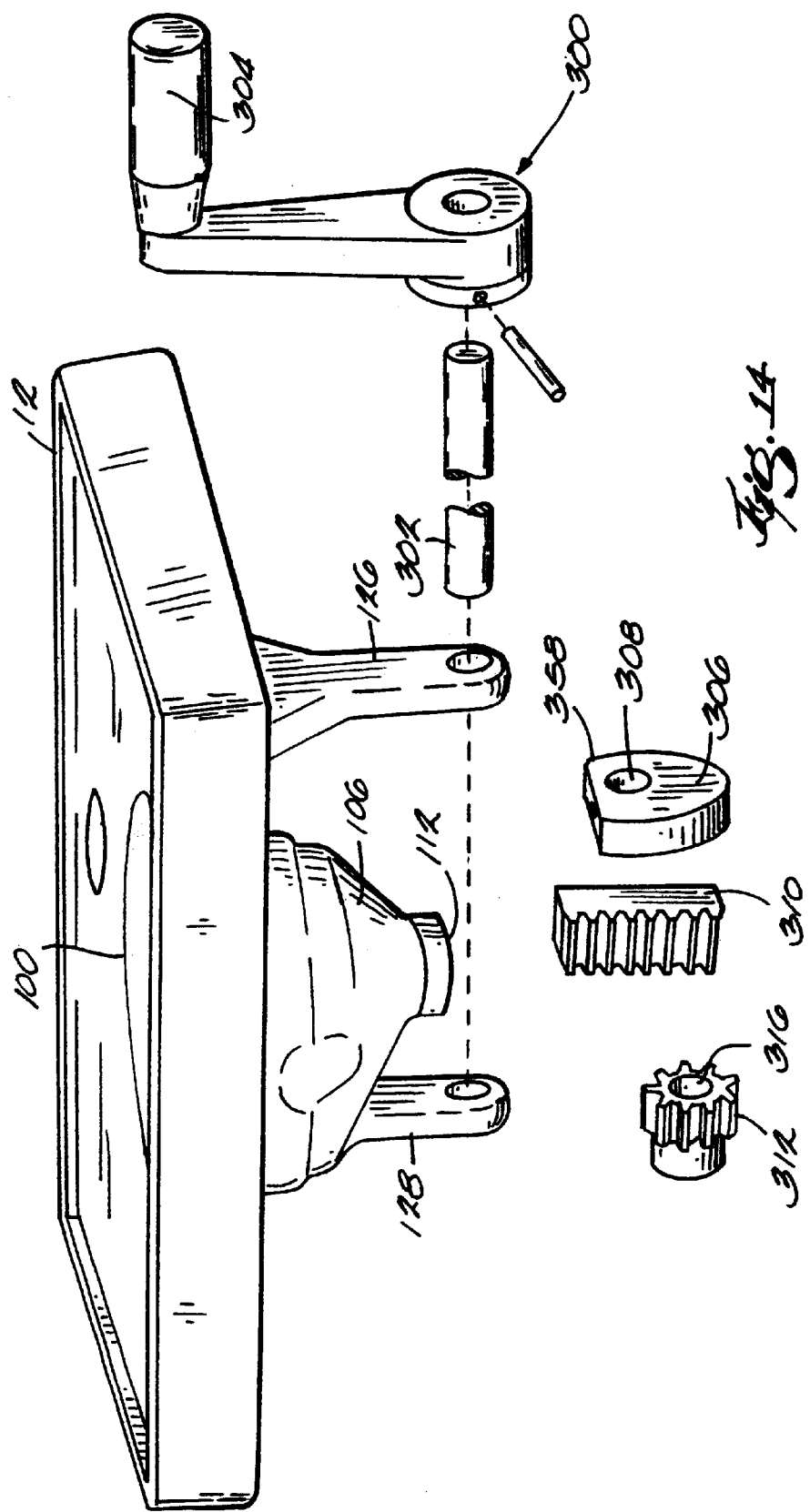
FIG. 14 is an exploded perspective view of the casting and a cam assembly.

The drain conduit 50 is actuated between the first position and the second position using an actuation mechanism, such as a cam assembly 300, as best shown in FIGS. 14 and 15. Although the actuation mechanism is shown and described as the cam assembly 300, the actuation mechanism may also be an automated mechanism, including control buttons or switches for example. The cam assembly 300 includes a cam shaft 302 that is positioned in the apertures 130 of the legs 126 and 128 of the casting 12 for rotational support. The cam shaft 302 has one end onto which a movable mechanism, such as a handle 304, is mounted. The cam assembly 300 also includes a cam 306 having an aperture 308 through which the cam shaft 302 is positioned. An edge 358 of the cam 306 engages an inlet water valve 24 (as shown schematically in FIG. 15 and as described in detail below).

The cam assembly 300 further includes a rack 310 and a pinion or spur gear 312. As shown in FIGS. 6 and 7, the rack 310 is mounted to a vertical member 318 that includes an elongated aperture 314 through which the main conduit portion 60 of the drain conduit 50 is rigidly positioned. The spur gear 312 includes an aperture 316 through which the cam shaft 302 is rigidly positioned. Accordingly, upon rotation of the handle 304, the cam shaft 302 is rotated, which in turn rotates the spur gear 312. The spur gear 312 cooperates with the rack 310 in order to raise or lower the drain conduit 50 between the first position and the second position. Thus, the rack 310 and spur gear 312 engage and move the drain conduit 50 reciprocally and longitudinally.

FIG. 15 is a schematic illustration of the cam assembly 300 and its relationship to the drainage station 10. Preferably, the drain station 10 uses water pressure and a venturi valve 22 to create negative pressure to drain or empty the bodily fluid from the container 14. Specifically, a water supply 18 is utilized. A water supply line 20 extends between the water supply 18 and the venturi valve 22. The inlet water valve 24 is disposed along the water supply line 20 between the water supply 18 and the venturi valve 22.

As shown schematically in FIG. 15, in addition to being coupled to the drain conduit 50, the cam assembly 300 is also coupled to the inlet water valve 24 in order to selectively provide water from the water supply 18 to the drainage station 10. Specifically, the edge 358 in the cam 306 engages a piston 360 (as best shown in FIGS. 15 and 16) of the inlet water valve 24 in order to open the inlet water valve 24. The piston 360 of the inlet water valve 24 is normally closed, i.e., the piston 360 is biased toward the closed position, so that when the edge 358 is released from engaging the piston 360, the piston 360 automatically returns to the closed position. The edge 358 does not engage the piston 360 and the inlet water valve 24 is closed when the drain conduit 50 is in the first or initial position. The edge 358 engages the piston 360 to open the inlet water valve 24 when the drain conduit 50 is in the second or operating position.

As shown schematically in FIG. 15 and as illustrated in FIGS. 10–13, a vacuum line 34 extends between the venturi valve 22 and the interior 32 of the drainage reservoir. As water passes through the venturi valve 22, the vacuum line 34 creates a vacuum in the interior 32 of the drainage reservoir 30 in order to hold the container 14 in the recess 100 of the casting 12. Thus, a user is prevented from removing the container 14 from the recess 100 while the container 14 is being drained. The vacuum line 34 also creates a vacuum in the interior 32 of the drainage reservoir 30 in order to drain the bodily fluid from the container 14.

Figure 18:
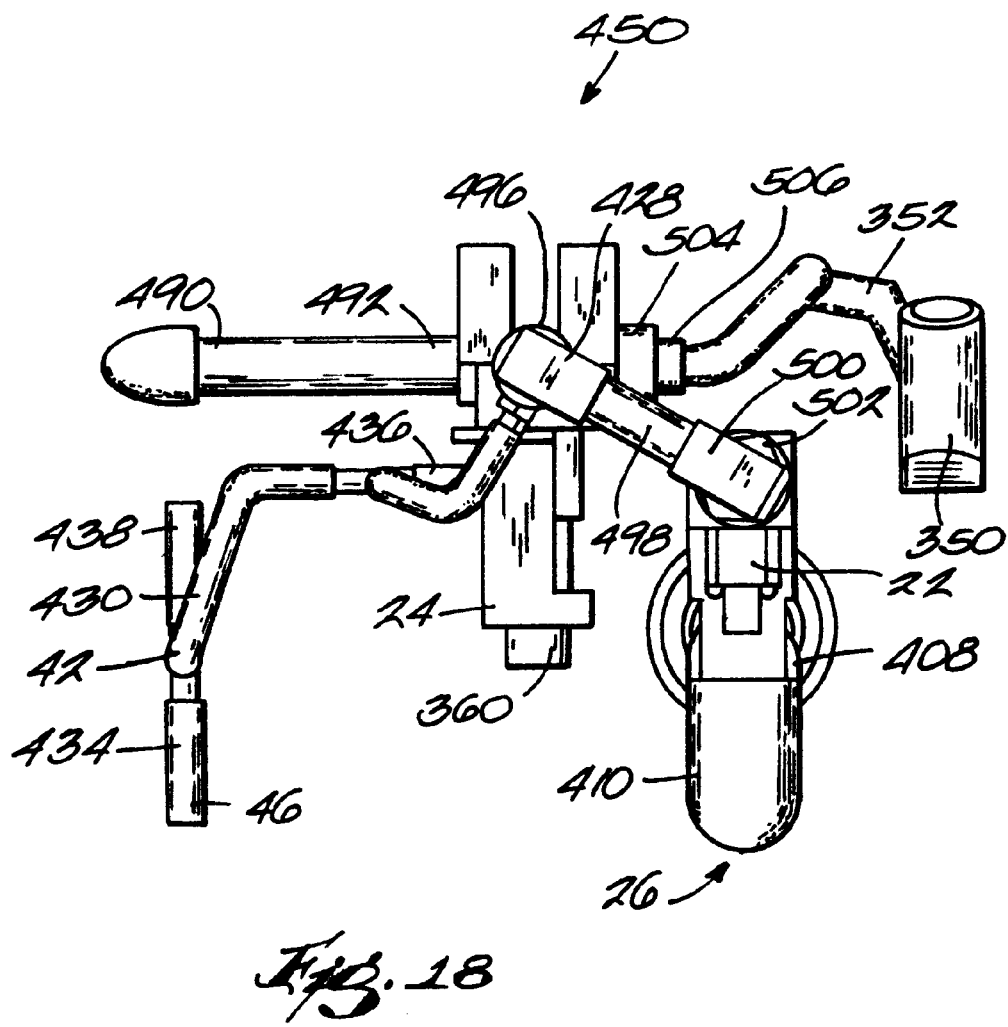
FIG. 18 is a top view of the water supply plumbing assembly and the water drainage plumbing assembly.

The water supply line 20 shown in FIG. 15 is embodied by a water supply assembly 450, as illustrated in FIGS. 16–18. The water supply assembly 450 includes the inlet water valve 24, which is preferably coupled to a hospital water system (not shown) via a conventional water pipe. A capped hose 490 is coupled to an input 492 of the inlet water valve 24. A first output 494 of the inlet water valve 24 is coupled to tee 428 by bushing 496. The tee 428 is coupled to a hose 498 which is coupled to tee 500. The tee 500 is coupled to the venturi valve 22 via a bushing 502. A second output 504 of the inlet water valve 24 is coupled to a sprayer hose 352 via a bushing 506.

As shown schematically in FIG. 15, a water drainage line 26 extends between the venturi valve 22 and the upper drainage assembly 258, which is ultimately in communication with the sanitary sewer system 28. As illustrated in FIGS. 16–18, the water drainage line 26 is embodied by a water drainage plumbing assembly 400. Preferably, the water drainage plumbing assembly 400 is also comprised of various PVC components. The water drainage plumbing assembly 400 includes socket 402, pipe 404, elbow 406, pipe 408, elbow 410, pipe 412, ell 414, pipe 416, ell 418, pipe 420, union 422, and pipe 424. As shown in FIGS. 1 and 10, pipe 424 is coupled to elbow 440. Elbow 440 is coupled to adapter 442 which is coupled to the second input 282 of the wye connector 280, which leads to the lower drainage assembly 290 and the sanitary sewer system 28.

Figure 12:
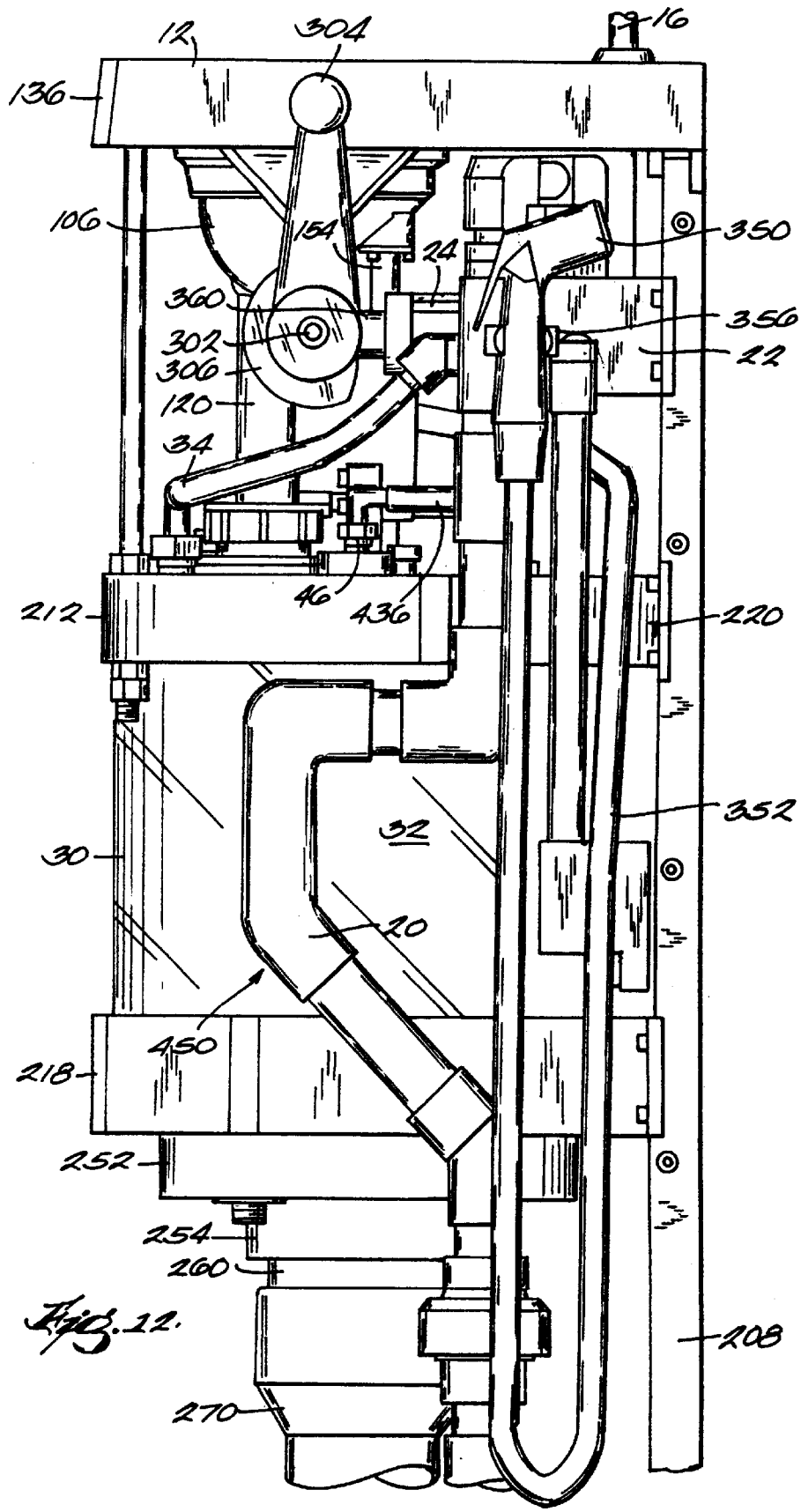
FIG. 12 is a side sectional view of the medical apparatus with the cabinet cover removed.
Figure 13:
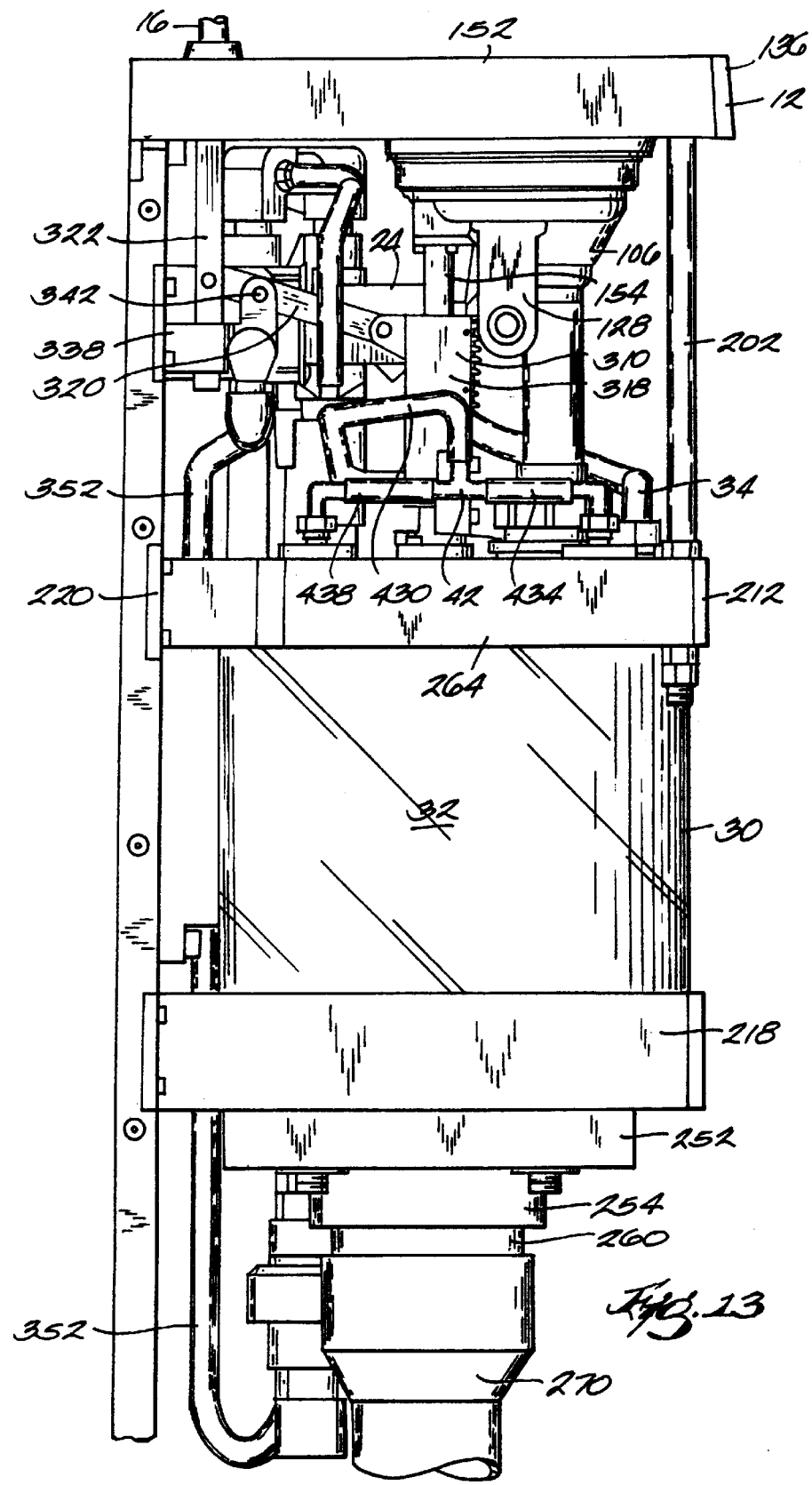
FIG. 13 is a side sectional view of the medical apparatus with the cabinet cover removed.

As shown schematically in FIG. 15, an emergency drain line 36 extends between the emergency drain port 112 of the casting 12 and the interior 32 of the drainage reservoir 30. As illustrated in FIGS. 12 and 13, the emergency drain line 36 is embodied by an emergency drain pipe 154 that extends from the emergency drain port 112 to the interior 32 of the drainage reservoir 30. The emergency drain line 36 ensures that if the drainage conduit 50 becomes blocked, any bodily fluid in the recess of the casting 12 does not overflow the recess 100, but rather drains into the drainage reservoir 30.

As shown schematically in FIG. 15, a water spray line 42 extends from a portion of the water supply line 20 between the inlet water valve 24 and the venturi valve 22 to the interior 32 of the drainage reservoir 30. Preferably, the water spray line 42 terminates in the interior 32 of the drainage reservoir 30 in one or more spray heads 46. As illustrated in FIGS. 16–19, the water spray line 42 is embodied by tee 428, hose 430, tee 432, first spray hose 434, second spray hose 436, and third spray hose 438. A spray head 46 is coupled to each one of the spray hoses 434, 436, and 438.

As shown in FIGS. 1, 6, 7, and 10, the drain station 10 also preferably includes a hold-down device 16, which engages the container 14 when the container 14 is positioned in the casting 12. The casting 12 includes an aperture 144 through which a vertical shaft 322 for the hold-down device 16 is movably positioned. The top end of the vertical shaft 322 is movably coupled within an aperture 346 of a horizontal member 324. As shown in FIGS. 1 and 10, a male-threaded pin 348 is positioned within a female-threaded aperture 354 in the horizontal member 324. The pin 348 is rotated until the pin 348 engages the vertical shaft 322 in order to secure the horizontal member 324 at a designated position along the vertical shaft 322. For example, the horizontal member 348 may be secured via the pin 348 in a higher position along the height of the vertical shaft 322 for a larger container 14 than for a smaller container 14. Preferably, the vertical shaft 322 is marked or labeled with designated positions for the horizontal member 324 for one or more standard-sized containers 14.

Referring to FIGS. 6 and 7, the horizontal member 324 includes a first recess 326 within which a spring 328 is positioned. The horizontal member 324 also includes a second recess 330 within which a flap 332 is secured via a pin 334. The flap 332 includes a notch 336 within which a top edge of the container 14 may be positioned. The spring 328 biases the flap 332 in a downward direction onto the top edge of the container 14. A slide plate 344 is also coupled to the top of the vertical shaft 322 in order to support the hold-down device 16 and to keep the hold-down device 16 from bending.

As best shown in FIGS. 6 and 7, the cam assembly 300 is coupled to the hold-down device 16. Specifically, a first end of a linkage 320 is rotatably coupled to the vertical member 318, which is rigidly coupled to the rack 310. The linkage 320 is also rotatably coupled at a pivot point 342 to a bracket 338. The bracket 338 is rigidly coupled to a horizontal member 292 coupled between the rear vertical support members 206 and 208. The bracket 338 includes an annular wall 340 within which the vertical shaft 322 is movably positioned. A second end of the linkage 320 is rotatably coupled to the vertical shaft 322.

As shown in FIG. 6, when the drainage conduit 50 is in the first position, the linkage 320 pivots about point 342 so that the vertical shaft 322 is moved upwardly. A container 14 may then be inserted into the recess 100 of the casting 12. The top edge of the container 14 is positioned adjacent to the notch 336 of the flap 332 of the hold-down device 16. As shown in FIG. 7, when the drainage conduit 50 is in the second position, the linkage 320 pivots about point 342 so that the vertical shaft 322 is moved downwardly. The notch 336 of the flap 332 then engages the top edge of the container 14 in order to secure the container 14 within the recess 100 of the casting 12. Also, it should be understood that, in alternative embodiments of the invention, the hold down device 16 can be omitted. Moreover, in other embodiments, the hold down device 16 may have other configurations, such as a magnetic device that engages a corresponding magnetic portion of the container 14.

As shown in FIGS. 1 and 10, the drainage station 10 further includes a manual sprayer 350 that is positioned adjacent to and releasably secured via a bracket 356 to the cabinet cover 140. As shown in FIG. 16, a sprayer hose 352 extends between the sprayer 350 and the second outlet 504 of the inlet water valve 24. The sprayer 350 is used by the user to optionally spray fluid into the container 14 or into the recess 100 of the casting 12 in order to wash any remaining bodily fluid out of the container 14 and through the drain port 114 of the casting 12 into the drainage reservoir 30.

Referring primarily to FIGS. 6, 7, and 15, the drainage station 10 is operated as follows. When the drain station 10 is not in use emptying a container 14, the reservoir plug 56 is positioned below the reduced-diameter portion 30C of the drainage reservoir 30, thereby leaving the interior 32 of the drainage reservoir 30 in communication with the outlet 250 and the sanitary sewer system 28. Further, the inlet water valve 24 is closed so that there is no water running through the drainage station 10.

When a user desires to drain a container 14, the user positions the hold-down device 16 by sliding the horizontal member 324 along the length of the vertical shaft 322 according to the size of the container 14 and then securing the pin 348. The user then places the container 14 in the recess 100 of the casting 12, such that the top edge of the container 14 is adjacent the hold-down device 16 and such that a keyway (not shown) on the container 14 aligns with the key 110 of the casting 12. Thus, the container 14 is oriented in the recess 100 such that a drain in the container 14 is positioned adjacent the tool 62. In addition, a cap (not shown) on the cover (not shown) of the container 14 is opened so that the fluid will not be vapor locked within the container 14.

As best shown in FIG. 15, the drain includes a cylindrical wall 90 that defines a drain port 92 that is preferably generally circular and located at the bottom of the container 14. A cap or cover 94 is positioned over the drain port 92. Preferably, the cap 94 is formed such that the material is thinner around the periphery of the cap 94 than the remainder of the cap 94 or the wall 90. The wall 90 and the cap 94 are also preferably integral with the container 14 so as to define a molded-in drain. In the first or initial position, as shown in FIG. 6, the tool 62 is spaced from the cap 94 and the cap 94 covers or blocks the drain port 92 to prevent fluid from exiting the container 14 via the drain port 92.

The user then pivots the handle 304 a quarter turn, approximately 90 degrees, toward him or herself to a first position. When the user rotates the handle 304, water flow from the water supply 18 through the water supply line 20 (i.e., the water supply assembly 450) is initiated. Specifically, as the cam shaft 302 rotates a quarter turn, the cam 306 is rotated. The edge 358 of the cam 306 engages the piston 360 of the normally-closed, inlet water valve 24 in order to push the piston 360 inward to open the inlet water valve 24. Water from the water supply 18 passes through the open inlet water valve 24 along the water supply line 20 (i.e., water supply assembly 450) and is partially diverted to the one or more spray heads 46 in the interior 32 of the drainage reservoir 30 via the water spray line 42 (i.e., tee 428, hose 430, tee 432, first spray hose 434, second spray hose 436, and third spray hose 438). The spray heads 46 spray water in order to dilute infectious waste in the drainage reservoir 30, rinse the drainage reservoir 30, and reduce the foaming of infectious waste in the drainage reservoir 30. The remainder of the water from the water supply 18 that is not diverted travels to and through the venturi valve 22 (via tee 428, hose 498, and tee 500) and then travels along the water drainage line 26 (i.e., water drainage plumbing assembly 400) to the sanitary sewer system 28.

Thus, with the inlet water valve 24 turned on, water can flow from the water supply 18, through the water supply line 20 (i.e., the water supply assembly 450), through the inlet water valve 24, through the venturi valve 22, and through the water drainage line 26 (i.e., the water drainage plumbing assembly 400). As the water passes through the venturi valve 22, a vacuum is generated in the interior 34 of the drainage reservoir 30 through the vacuum line 34 creating a suction force through the drain passageway 120 to hold the container 14 in place in the recess 100. This suction force helps prevent a user from accidentally removing the container 14 from the recess 100 when fluid is draining from the container 14.

In addition to the cam 306 engaging the piston 360 when the cam shaft 302 rotates a quarter turn, the spur gear 312 engages the rack 310 in order to move the drainage conduit 50 upwardly slightly, but not far enough to engage the bottom of the container 14.

As the handle 304 is rotated through the 90 degrees, the user can hear the water flow and the suction force created in the drain passageway 120. The user then continues to rotate the handle 304 another 90 degrees towards him or herself to a second position, for a total of 180 degrees of rotation, such that the cam assembly 300 moves to its second position, as shown in FIG. 7. Specifically, as the handle 304 is rotated, so is the cam shaft 302 and the cam 306. Therefore, the inlet water valve 24 remains in its on position during the second 90 degree rotation of the handle 304.

As for the hold-down device 16, the linkage 320 is moved by the vertical member 318 which is rigidly coupled to the rack 310. The linkage 320 in turn moves the vertical shaft 322 of the hold-down device 16 downwardly until the flap 332 of the horizontal member 324 engages the top edge of the container 14. The spring 328 biases the flap 332 into engagement with the top edge of the container 14.

As for the drainage conduit 50, rotation of the cam shaft 302 another 90 degrees, forces the drainage conduit 50 upwardly to the second or operating position, as shown in FIG. 7. The drainage conduit 50 is forced upwardly due to the spur gear 312 engaging the rack 310. As the drainage conduit 50 moves upwardly, the reservoir plug 56 is positioned into a sealing relationship with the outlet 250 of the drainage reservoir 30. Thus, the interior 32 of the drainage reservoir 30 is sealed and communication between the drainage reservoir 30 and the sanitary sewer 28 is not allowed.

Referring to FIG. 7, the upward movement of the drainage conduit 50 moves the tool 62 upwardly to contact the container 14. As the tool 62 moves upwardly, the first portion 76 of the tool 62 contacts the cap 94. Further upward movement of the tool 62 begins to break or sever the connection between the wall 90 and the cap 94 at a location adjacent the first portion 76. Continued upward movement of the tool 62 continues to break the connection between the wall 90 and the cap 94 around almost, but not all of, the periphery of the cap 94. Because the second and third portions 78 and 80, respectively, of the tool 62 terminate in the plane 84 that is spaced from the plane 82 in which the first portion 76 terminates, the connection between the cap 94 and the wall 90 around the periphery of the cap 94 is not completely severed. Instead, a hinge 96 remains intact so that the cap 94 does not completely release from the container 14. As the tool 62 ceases its upward movement, the second and third portions 78 and 80, respectively, cause the cap 94 to pivot about the hinge 96 to a generally vertical position, termed the second or draining position. The tool 62 holds or fixes the cap 94 in this second position and does not allow the cap 94 to move within the interior of the container 14.

An advantage of a cap 94 not completely severing from the container 14 is that the cap 94 can be positioned and maintained in that position so as not to block the drainage of the fluid through the tool 62. If the cap 94 completely severed from the container 14, the combination of the fluid flow and suction can lodge the cap 94 over the tool 62 and block or partially block fluid flow through the passageway 66 of the tool 62. However, it should be noted that if desired, the tool 62 could completely sever the cap 94 from the container 14.

Accordingly, with the cap 94 partially severed and pivoted to its vertical position, fluid flows from the container 14, through the central passageway 66 of the tool 62, through the main conduit portion 60, and through the cutout portion 58 into the drainage reservoir 30. Fluid drains from the container 14 because the water flowing through the venturi valve 22 creates a suction force in the drainage reservoir 30 to draw fluid from the container 14. If desired, the user can remove any lid on the container 14 and use the sprayer 350 to clean the interior of the container 14. The bodily fluids from the container 14 and the fluid from the sprayer 350 collect in the drainage reservoir 30, because the reservoir plug 26 prevents the fluid from flowing through the outlet 250.

As the bodily fluid drains into the drainage reservoir 30, the gasket 118 prevents the fluid from flowing into the recess 100 of the casting 12. However, should any fluid flow into the bottom of the recess 100, the seal 108 prevents the fluid from overflowing the recess 100. Further, the emergency drainage port 112 is used as a secondary drainage port in communication with the drainage reservoir 30 via the emergency drain pipe 154.

After the fluid has drained from the container 14 into the drainage reservoir 30, the user rotates the handle 304 back to its starting position, i.e., 180 degrees away from the user. When the user rotates the handle 304 to its original position, the cam shaft 302 and the cam 306 are rotated. The edge 358 of the cam 306 disengages from the piston 360 of the inlet water valve 24, so that the normally-closed, inlet water valve 24 returns to the closed position.

Moreover, when the user rotates the handle 304 to its original position, the spur gear 312 engages the rack 310 in order to move the drainage conduit 50 downwardly. When the drainage conduit 50 moves downwardly, the reservoir plug 56 moves out of a sealing relationship with the reduced-diameter portion 30C of the drainage reservoir 30. The bodily fluid in the interior 32 of the drainage reservoir 30 then drains through the outlet 250, the upper drainage assembly 258, the lower drainage assembly 290, and into the sanitary sewer system 28. Due to the generally vertical orientation of the drain station 10 components, the bodily fluid drains out of the drain station 10 by gravity. Thus, check valves are not necessary to prevent the backward flow of the bodily fluid.

As can be seen, the bodily fluid from the container 14 is not mixed with the water entering and exiting the venturi valve 22 while within the drainage station 10. The bodily fluid drains to the sanitary sewer system 28 via the upper drainage assembly 258. The water entering the venturi valve 22 thereafter exits the venturi valve 22 along the water drainage line 26 (i.e., water drainage plumbing assembly 400). The bodily fluid exiting the drainage reservoir 30 through the upper drainage assembly 258 and the water exiting the venturi valve 22 through the water drainage plumbing assembly 400 meet at the lower drainage assembly 290 and travel to the sanitary sewer system 28.

When the user rotates the handle 304 to its original position, the vertical shaft 322 of the hold-down device 16 moves upwardly. The user can then easily remove the container 14 from beneath the flap 332 of the horizontal member 324 and can remove the container 14 out of the recess 100 of the casting 12. The user can then dispose of the container 14.

While several drain arrangements and drain opening devices have been disclosed, it should be understood that other types of drains and other devices for opening drains are within the scope of the invention.

Various features of the invention are set forth in the following claims, wherein the term "container" includes suction canisters, urine collectors, chest drainage devices and other types of containers for collecting body fluids.

We claim:

1. A medical apparatus for draining bodily fluid held in a container, the apparatus comprising:

a support area that is adapted to removably support the container;

a drainage reservoir having an inlet in communication with the support area and an outlet in communication with a drain, the drainage reservoir being adapted to collect the bodily fluid drained from the container before the bodily fluid flows into the drain; and a drainage conduit positioned within the drainage reservoir, the drainage conduit having a first end movably positioned in the inlet, the first end including a tool that is actuable to alter the container such that the bodily fluid held in the container drains from the container.

2. The medical apparatus of claim 1, wherein the drainage reservoir includes a first portion having a generally cylindrical shape coupled to a second portion having a tapered shape, and wherein the second portion is tapered toward the outlet so that the bodily fluid flows toward the outlet.

3. The medical apparatus of claim 1, and further comprising a spray head in communication with the drainage reservoir, the spray head being adapted to spray fluid into the drainage reservoir.

4. The medical apparatus of claim 1, wherein the drain is coupled to a sewer system.

5. A method of draining bodily fluid from a container, the method comprising:

positioning the container in a support area that is adapted to removably support the container;

providing a drainage conduit positioned within the drainage reservoir, the drainage conduit having a first end including a tool movably positioned in the inlet;

moving the drainage conduit into a first position in which the tool is actuated to alter the container;

draining the bodily fluid from the container;

collecting the bodily fluid drained from the container into a drainage reservoir; and releasing the bodily fluid collected in the drainage reservoir into a drain.

6. The method of claim 5, and further comprising spraying a fluid into the drainage reservoir.

7. The method of claim 6, wherein spraying a fluid into the drainage reservoir includes spraying water into the drainage reservoir.

8. The method of claim 5, wherein the drain is coupled to a sewer system, and wherein releasing the bodily fluid collected in the drainage reservoir into a drain includes releasing the bodily fluid into the sewer system.

9. A medical apparatus for draining bodily fluid held in a container, the apparatus comprising:

a support area that is adapted to removably support the container;

a drainage reservoir having an inlet in communication with the support area and an outlet in communication with a drain; and a drainage conduit positioned within the drainage reservoir, the drainage conduit having a first end movably positioned in the inlet, the first end including a tool that is actuable to alter the container such that the bodily fluid held in the container drains from the container, and a second end having a reservoir plug removably positioned in the outlet in order to selectively prevent the bodily fluid from flowing out of the drainage reservoir and into the drain.

10. The medical apparatus of claim 9 wherein the drainage conduit is movable between a first position in which the tool is not actuated to alter the container and the reservoir plug is not positioned in the outlet so that the bodily fluid is allowed to flow into the drain, and a second position in which the tool is actuated to alter the container and the reservoir plug is positioned in the outlet so that the bodily fluid is collected in the drainage reservoir.

11. The medical apparatus of claim 9, wherein the second end of the drainage conduit includes a cutout portion that is adapted to allow the bodily fluid to flow out of the drainage conduit and into the drainage reservoir.

12. The medical apparatus of claim 11, wherein the cutout portion has an oval shape.

13. A method of draining bodily fluid from a container, the method comprising:

positioning the container in a support area that is adapted to removably support the container;

moving a drainage conduit into a first position in which a tool coupled to a first end of the drainage conduit alters the container and a reservoir plug coupled to a second end of the drainage conduit is positioned in an outlet of a drainage reservoir so that the bodily fluid drains from the container and is collected in the drainage reservoir; and moving the drainage conduit into a second position in which the reservoir plug is removed from the outlet so that the bodily fluid flows from the drainage reservoir into a drain.

14. A method of draining bodily fluid from a container, the method comprising:

positioning the container in a support area that is adapted to removably support the container;

providing a drainage reservoir having an inlet in communication with the support area and an outlet in communication with a drain;

providing a drainage conduit positioned within the drainage reservoir, the drainage conduit having a first end including a tool movably positioned in the inlet and a second end including a reservoir plug removably positioned in the outlet;

moving the drainage conduit into a first position in which the tool is actuated to alter the container and the reservoir plug is positioned in the outlet so that the bodily fluid drains from the container and collects in the drainage reservoir; and moving the drainage conduit into a second position in which the tool is not actuated to alter the container and the reservoir plug is not positioned in the outlet so that the bodily fluid flows from the drainage reservoir into the drain.

15. A medical apparatus for draining bodily fluid held in a container, the apparatus comprising:

a support area that is adapted to removably support the container;

a drainage reservoir having an inlet in communication with the support area and an outlet; and a drainage pipe in communication with the outlet of the drainage reservoir, at least a portion of the drainage pipe having a diameter greater than the diameter of the outlet the drainage pipe being coupled to a sewer system.

16. The medical apparatus of claim 15, wherein the drainage reservoir and the drainage pipe are in substantially vertically aligned positions so that the bodily fluid flows downward by gravity.

17. A medical apparatus for draining bodily fluid held in a container, the apparatus comprising:

a support area that is adapted to removably support the container;

a drainage reservoir having an inlet in communication with the support area and an outlet; and a drainage pipe in communication with the outlet of the drainage reservoir, at least a portion of the drainage pipe having a diameter greater than the diameter of the outlet, wherein the drainage pipe is coupled to a sewer system, and wherein the drainage pipe has a diameter greater than the diameter of the outlet until the drainage pipe reaches the sewer system so that once the bodily fluid flows through the outlet the bodily fluid flows without restriction to the sewer system.

18. A medical apparatus for draining bodily fluid held in a container, the apparatus comprising:

a support area that is adapted to removably support the container; and a drainage reservoir in communication with the support area, the drainage reservoir being adapted to collect the bodily fluid drained from the container, and the drainage reservoir being constructed of a transparent material so that the bodily fluid being collected in the drainage reservoir can be viewed from outside of the drainage reservoir, the drainage reservoir being coupled to a sewer system.

19. The medical apparatus of claim 18, and further comprising a drainage conduit positioned in communication with the support area and positioned within the drainage reservoir, and wherein the drainage conduit includes a cutout portion that is adapted to allow the bodily fluid to flow out of the drainage conduit and into the drainage reservoir.

20. The medical apparatus of claim 19, wherein the cutout portion is positioned within the drainage reservoir so that the bodily fluid flowing out of the cutout portion can be viewed from outside the drainage reservoir.

21. The medical apparatus of claim 19, wherein the cutout portion has an oval shape.

22. A medical apparatus for draining bodily fluid held in a container, the apparatus comprising:

a support area that is adapted to removably support the container;

a drainage reservoir in communication with the support area and a drain; and a venturi valve coupled between a water supply and the drain, the venturi valve being in communication with the drainage reservoir to generate a vacuum in order to drain the bodily fluid from the container, the water passing through the venturi valve remaining isolated from the bodily fluid passing through the drainage reservoir until the water and the bodily fluid reach the drain.

23. The medical apparatus of claim 22, wherein the venturi valve generates a vacuum in the support area to hold the container in the support area.

24. The medical apparatus of claim 22, wherein the drain is coupled to a sewer system.

25. A medical apparatus for draining bodily fluid held in a container, the apparatus comprising:

a first fluid path including
a support area that is adapted to removably support the container, a drainage reservoir coupled to the support area, and
a drain coupled to the drainage reservoir; and second fluid path including
a water supply, and
a venturi valve coupled to the water supply and the drain, the venturi valve being in communication with the drainage reservoir in order to generate a vacuum to drain the bodily fluid from the container;
wherein the bodily fluid flowing through the first fluid path is isolated from water flowing through the second fluid path until the bodily fluid and the water reach the drain.

26. The medical apparatus of claim 25, wherein the venturi valve is in communication with the support area in order to generate a vacuum to hold the container in the support area.

27. The medical apparatus of claim 25, wherein the drain is coupled to a sewer system.

28. A method of draining bodily fluid from a container, the method comprising:

positioning the container in a support area that is adapted to removably support the container;

providing a drainage reservoir in communication with the support area and a drain;

generating a vacuum in the drainage reservoir by passing water through a venturi valve in communication with the drainage reservoir in order to drain the bodily fluid from the container into the drainage reservoir;

releasing the bodily fluid from the drainage reservoir into the drain; and preventing the water passing through the venturi valve from mixing with the bodily fluid until the water and the bodily fluid reach the drain.

29. The method of claim 28, and further comprising generating a vacuum in the support area by passing water through the venturi valve in communication with the support area in order to hold the container in the support area.

30. A medical apparatus for draining bodily fluid held in a container, the apparatus comprising:

a support area that is adapted to removably support the container;

a drainage reservoir having an inlet in communication with the support area in order to receive the bodily fluid drained from the container and an outlet; and a drainage pipe having a first end in communication with the inlet of the drainage reservoir and a second end in communication with the outlet of the drainage reservoir in order to release the bodily fluid from the drainage reservoir into a drain;

the bodily fluid flowing through the support area, the drainage reservoir, and the drainage pipe and into the drain without the use of a check valve.

31. The medical apparatus of claim 30, wherein the drainage reservoir and the drainage pipe are in substantially vertically aligned positions so that the bodily fluid flows downward by gravity.

32. A medical apparatus for draining bodily fluid held in a container, the apparatus comprising:

a support area that is adapted to removably support the container;

a drainage reservoir having an inlet in communication with the support area and an outlet in communication with a drain, the drainage reservoir being adapted to collect the bodily fluid drained from the container before the bodily fluid is released into the drain, and the drainage reservoir being constructed of a transparent material;

a drainage conduit positioned within the drainage reservoir, the drainage conduit having a first end including a tool movably positioned in the inlet, and a second end having a reservoir plug removably positioned in the outlet and a cutout portion that is adapted to allow the bodily fluid to flow out of the drainage conduit and into the drainage reservoir;

a venturi valve coupled between a water supply and the drain in order to generate a vacuum in the drainage reservoir in order to drain the bodily fluid from the container; and a cam assembly having a first position in which the tool is not actuated to alter the container, the reservoir plug is not positioned in the outlet, and the venturi valve is inactive, and a second position in which the tool is actuated to alter the container, the reservoir plug is positioned in the outlet, and the venturi valve generates the vacuum.

\* \* \* \* \*